United States Patent
Fluri et al.

(10) Patent No.: US 11,154,715 B2
(45) Date of Patent: Oct. 26, 2021

(54) METHODS FOR ELECTRICAL STIMULATION OF THE MESENCEPHALIC LOCOMOTOR REGION FOR THE TREATMENT OF GAIT IMPAIRMENT AFTER STROKE USING A NEUROSTIMULATION DEVICE

(71) Applicant: JULIUS-MAXIMILIANS-UNIVERSITÄT WÜRZBURG, Würzburg (DE)

(72) Inventors: Felix Fluri, Bottmingen (CH); Jens Volkmann, Würzburg (DE)

(73) Assignee: Julius-Maximilians-Universität Würzburg, Würzburg (DE)

(*) Notice: Subject to any disclaimer, the term of this patent is extended or adjusted under 35 U.S.C. 154(b) by 242 days.

(21) Appl. No.: 16/393,834

(22) Filed: Apr. 24, 2019

(65) Prior Publication Data

US 2019/0321626 A1  Oct. 24, 2019

Related U.S. Application Data

(60) Provisional application No. 62/662,174, filed on Apr. 24, 2018.

(51) Int. Cl.
*A61N 1/36* (2006.01)
*A61N 1/05* (2006.01)

(52) U.S. Cl.
CPC ....... *A61N 1/36103* (2013.01); *A61N 1/0531* (2013.01); *A61N 1/36067* (2013.01); *A61N 1/36171* (2013.01); *A61N 1/0534* (2013.01); *A61N 1/36003* (2013.01); *A61N 1/36025* (2013.01); *A61N 1/36082* (2013.01)

(58) Field of Classification Search
None
See application file for complete search history.

(56) References Cited

U.S. PATENT DOCUMENTS 5,002,053 A * 3/1991 Garcia-Rill ........ A61N 1/36003
607/49

OTHER PUBLICATIONS

Fluri et al., "Stimulation of the Mesencephalic Locomotor Region for Gait Recovery After Stroke," ANN NEUROL 2017; 82:828-840. (Year: 2017).*
Mahlknecht et al., "Deep Brain Stimulation for Movement Disorders: Update on Recent Discoveries and Outlook on Future Developments," J. Neurology, 2015 262:2583-2589. (Year: 2015).*
Fidel Baizabal-Carvallo et al., "Low-frequency Deep Brain Stimulation for Movement Disorders," Parkinsonism and Related Disorders Clinic, Baylor College of Medicine, 31 (2016) 14-22 (Year: 2016).*
Fasano et al., "Treatment of Motor and Non-motor Features of Parkinson's Disease with Deep Brain Stimulation," The Lancet Neural, vol. 11, 429-442, May 2012. (Year: 2012).*

(Continued)

*Primary Examiner* — Kennedy Schaetzle
(74) *Attorney, Agent, or Firm* — Adriano & Associates

(57) ABSTRACT

Methods for treating, reducing or reversing a motor deficit in a subject after a stroke comprising administering continuous electrical stimulation to the mesencephalic locomotor region (MLR) of the subject under sufficient conditions so as to treat, reduce or reverse the motor deficit of the subject are provided.

29 Claims, 3 Drawing Sheets

(56) References Cited

OTHER PUBLICATIONS

Fluri F et al, Microelectrode guided implantation of electrodes into the subthalamic nucleus of rats for long-term deep brain stimulation. J Vis Exp. Oct. 2, 2015;(104). doi: 10.3791/53066—Exhibit 1.

Rattka M et al, A Novel Approach to Assess Motor Outcome of Deep Brain Stimulation Effects in the Hemiparkinsonian Rat: Staircase and Cylinder Test. J Vis Exp. May 31, 2016;(111). doi: 10.3791/53951—Exhibit 2.

Musacchio T et al, STN-DBS is neuroprotective in the A53T α-synuclein Parkinson's disease rat model. Ann Neurol. 2017;81:825-836—Exhibit 3.

Fluri F et al, Development of a head-mounted wireless microstimulator for deep brain stimulation in rats. J Neurosci Methods. 2017;291:249-256—Exhibit 4.

Fluri F et al, Continuous stimulation of the subthalamic nucleus improves skilled forelimb grasping after photothrombotic infarction in Wistar rats. Mov Dis. Jun. 2015, vol. 30, Suppl 1, pp. S271-S272, Abstract-# 686—Exhibit 5.

Musacchio T et al, Deep brain stimulation in the STN of a Parkinsonian rat model overexpressing human A53T α-synuclein in the substantia nigra—A proof of principle. Mov Dis. Jun. 2016, vol. 31, Suppl 2, pp. S23, Abstract-# 59—Exhibit 6.

Fluri F et al, Deep brain stimulation of the locomotor mesencephalic region in rats with lesioned sensorimotor cortex: A model of functional motor recovery after stroke. Mov Dis. Jun. 2016, vol. 31, Suppl 2, pp. S580, Abstract-# 1760—Exhibit 7.

Fluri F et al, Detection of activated motor circuits involved in gait restoration during stimulation of the mesencephalic locomotor region in a rat stroke model. European Stroke Journal 2017, vol. 2, Suppl, p. 222, Abstract# AS12-056—Exhibit 8.

Sehuhmann MK et al, Stimulation of the mesencephalic locomotor region attenuated neuronal loss and cytokine expression in the perilesional area of phothrombotic stroke in rats. European Stroke Journal 2018, vol. 3, Suppl 1, pp. 523, Abstract-# AS28-013—Exhibit 9.

\* cited by examiner

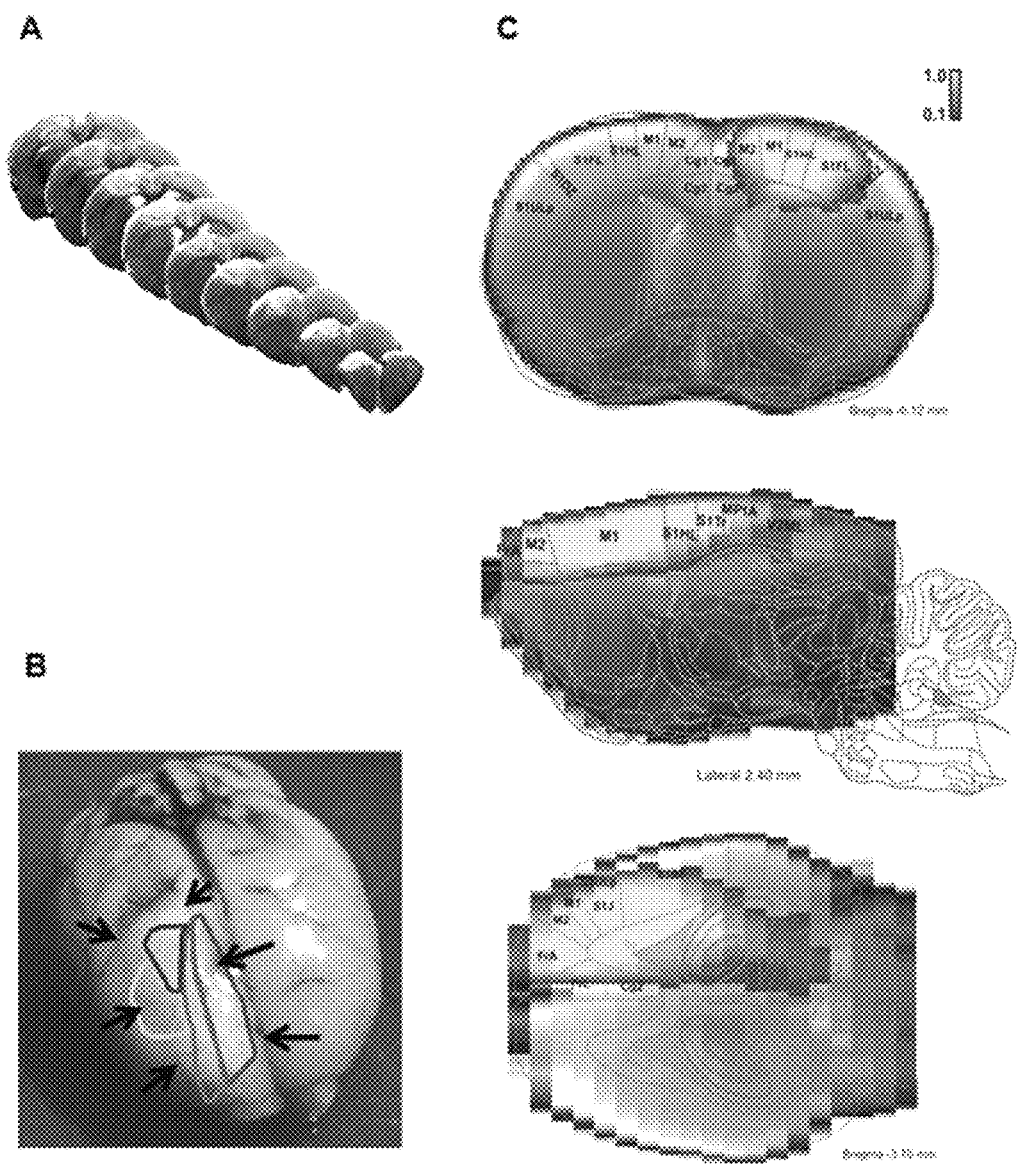
FIGURE 1a-c

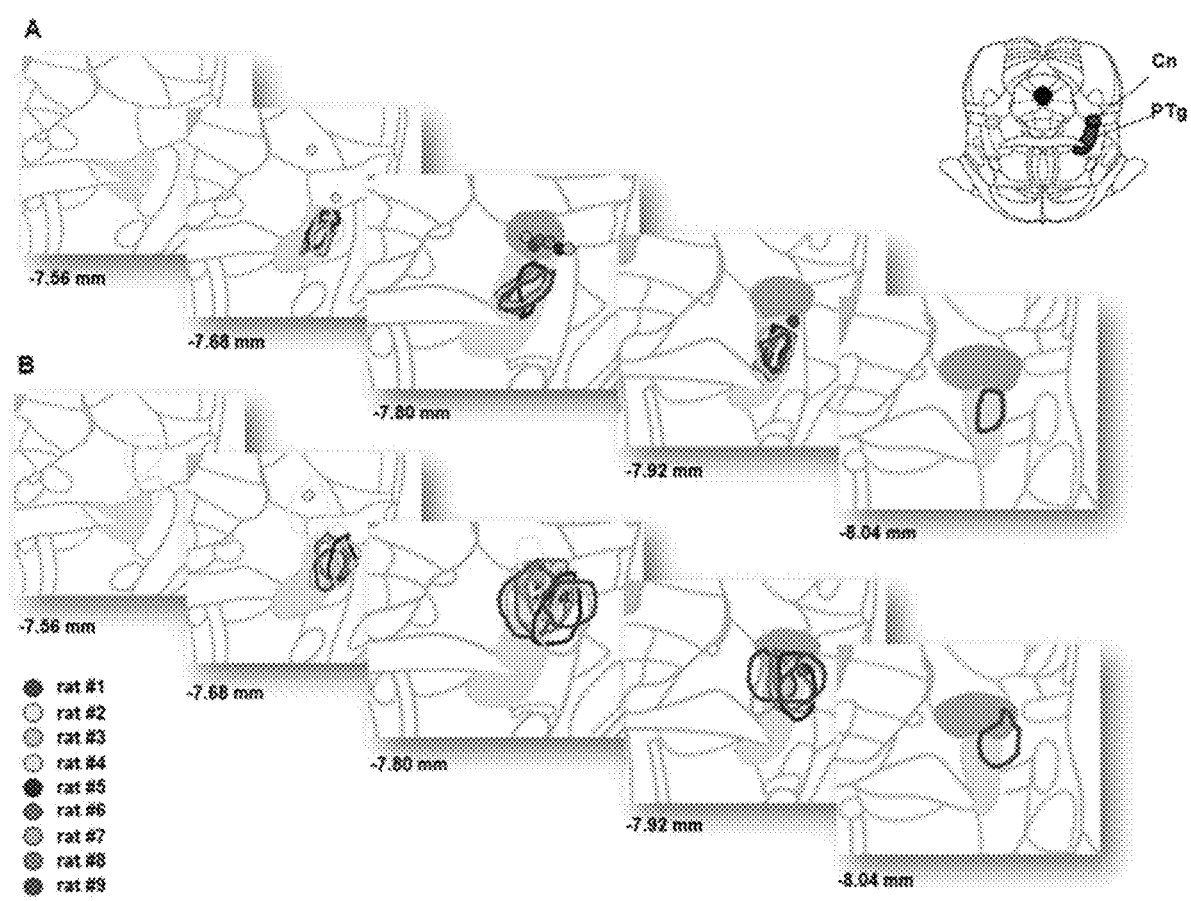
FIGURE 2a-b

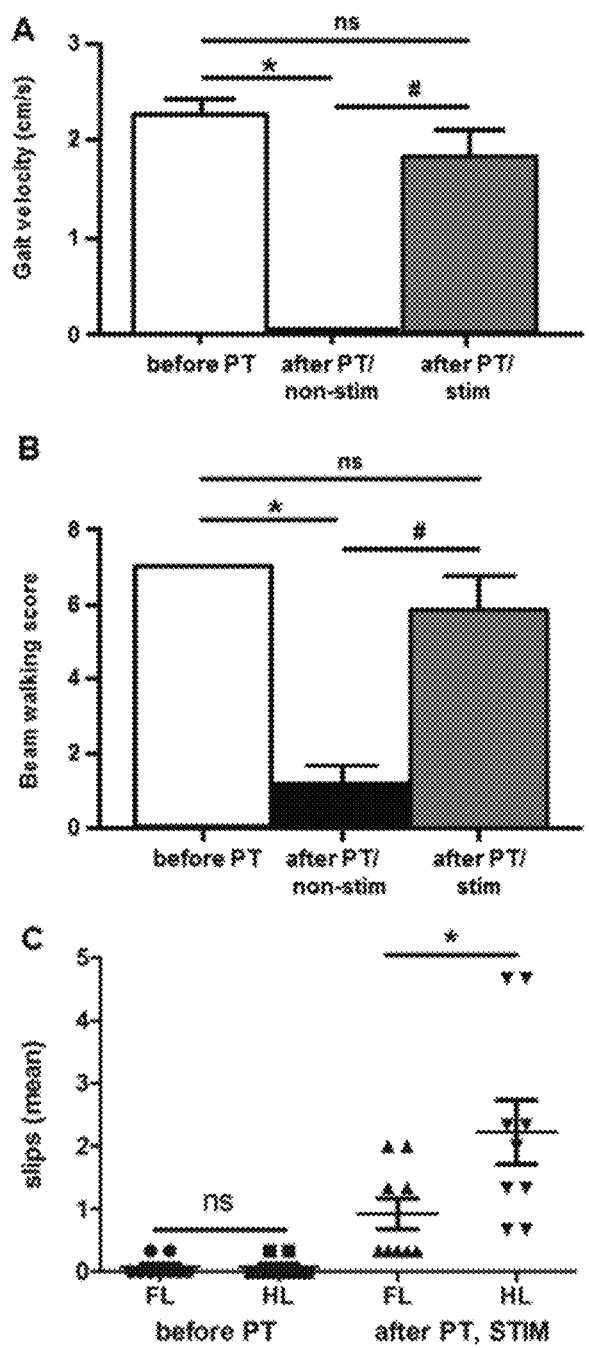
FIGURE 3a-c

METHODS FOR ELECTRICAL STIMULATION OF THE MESENCEPHALIC LOCOMOTOR REGION FOR THE TREATMENT OF GAIT IMPAIRMENT AFTER STROKE USING A NEUROSTIMULATION DEVICE

CROSS REFERENCE TO RELATED APPLICATIONS

The application claims priority to U.S. Provisional Application No. 62/662,174 filed Apr. 24, 2018, which is incorporated herein by reference in its entirety for all purposes.

Throughout this application various publications are referenced. The disclosures of these publications in their entireties are hereby incorporated by reference into this application in order to more fully describe the state of the art to which this invention pertains.

BACKGROUND OF THE INVENTION

Ischemic stroke is a severe acute neurological disease which results in a disruption of brain function, pathological cerebral oscillations and finally in neuronal cell death.[1] Spontaneous functional recovery from symptoms after ischemic stroke can be observed and is attributed to neuronal plasticity and cerebral remodeling.[2] There is growing evidence that structural and functional remodeling of the border zone close to the infarction or remote regions may change signaling within neuronal networks and contributes to functional improvement.[3] Rewiring of neuronal networks is thought to be mediated by electrochemical signals that—in turn—trigger different mechanisms involved in neuronal plasticity.

Several efforts have been undertaken to support recovery from stroke symptoms such as pharmacological, neuroprotective and revascularization treatments (i.e., intravenous thrombolysis, mechanical endovascular treatment) as well as physical therapy,[4] neurodevelopmental training or motor relearning programs.[5] However, the overall effect of physiotherapy in chronic stroke survivors is modest and there are no pharmacological or interventional alternatives.[7] Since the brain is an electrical organ, modulation of cerebral dysfunction might be achieved by an electromagnetic approach. In this context, transcranial magnetic stimulation (TMS)—a noninvasive method has been investigated in stroke survivors regarding its effect on lower or upper limb paresis.[8] However, a recently published Cochrane review concluded that current evidence does not support routine use of repetitive TMS to improve overall function after ischemic stroke.[9] Moreover, high frequency TMS carries potential risk and must be administered according to safety guidelines.[10]

Another technique is direct current stimulation (DCS), which can also be applied transcranially.[11] Yet, a Cochrane review combining wide-ranging transcranial DCS (tDCS) methods found only limited evidence that tDCS improves overall function in patients after stroke.[12] An unpublished study carried out by Buzsáki and coworkers raised considerable doubts about the efficacy of this method: based on measurements from electrodes inside cadavers, they found an absorption of electromagnetic waves of 90% in other words an electrical current twice as high as allowed for tDCS would be necessary to stimulate the firing of living neurons inside the skull.[13]

Levy and coworkers[14] have chosen another solution to apply high frequency stimulation to the motor cortex in patients with ischemic stroke. In their prospective multicenter study, stroke survivors with moderate to severe hemiparesis received electrical epidural motor cortex stimulation via implanted electrode over 6 weeks and were compared with stroke patients without this intervention. However, the primary end point, an improvement in motor function of the paretic upper limb, was similar in both, the stimulated and the control group.[14]

Noninvasive stimulating methods as well as the aforementioned approach of invasive epidural stimulation showed none or only a modest effect on motor symptoms in stroke patients. We present a new target site by which deep brain stimulation (DBS) technology might be applied to the improvement of gait disorders resulting from stroke.

The present invention addresses the technical and methodological problems applying DBS in patients with impaired mobility and provides guidance treatment of impaired mobility associated with a brain lesion such as gait impairment after stroke.

SUMMARY OF THE INVENTION

The invention provides methods for treating impaired mobility associated with a brain lesion in a subject comprising stimulation of mesencephalic locomotor region (MLR) of the subject in a sufficient amount or level so as to reverse impaired mobility in the subject, thereby treating impaired mobility associated with a brain lesion in the subject.

Additionally, the invention further provides methods for determining therapeutic efficacy of deep brain stimulation in restoring gait in a subject after experimentally induced stroke comprising: a) implantation of electrode ipsilateral or both, ipsilateral and contralateral to the stroke at mesencephalic locomotor region; b) administration of electrical stimulation; c) observation of locomotor behavior before and after electrical stimulation; d) comparison of observed locomotor behavior before and after electrical stimulation to determine if electrical stimulation increases and/or improves locomotor behavior; thereby, determining therapeutic efficacy of deep brain stimulation in restoring gait in an animal subject after experimentally induced stroke.

Also provided is a method for inhibiting, reversing and/or reducing a motor deficit in a subject after a stroke, comprising administering continuous electrical stimulation in a suitable amount or level to the mesencephalic locomotor region (MLR) of the subject under sufficient conditions so as to inhibit, reverse and/or improve the motor function of the subject, thereby reducing the motor deficit of the subject. The invention further provides a method for a rehabilitating subject suffering from a motor deficit as a result of a stroke by treating the motor deficits of the subject by using the method mentioned above.

The invention further provides a method for treating a motor deficit of a subject after a stroke comprising administering continuous electrical stimulation to the mesencephalic locomotor region (MLR) of the subject in a suitable amount or level such that the continuous electrical stimulation promotes movement so as to treat the motor deficit of the subject. The invention further provides a method for a rehabilitating subject suffering from a motor deficit as a result of a stroke by treating the motor deficits of the subject by using the method mentioned above.

The invention additionally provides kits for treating impaired mobility associated with a brain lesion in a subject comprising: (a) an electrode for administering electrical stimulation at mesencephalic locomotor region of the subject in a suitable amount or level; and (b) a label and instruction on treating subjects having impaired mobility associated with or as a result of a brain lesion as described herein.

BRIEF DESCRIPTION OF THE DRAWINGS

FIG. 1a-c: Visualization of the photothrombotic stroke and the electrode tip. (A) Representative coronal T2-weighted (T2w) magnetic resonance scans revealing the photothrombotic stroke (hyperintense area) in the right sensorimotor cortex of a rat brain. (B) Macroscopic view of a rat brain after removal from the skull. The black arrows indicate the photothrombotically induced lesion. Primary motor cortex (M1), blue framed; secondary motor cortex (M2), green framed; primary somatosensory cortex, forelimb, yellow framed; primary somatosensory cortex, hind limb, brown framed (according to Paxinos and Watson's rat brain atlas[18]). (C) Brain sections in 3 planes (coronal [top]; sagittal [middle]; horizontal [bottom]) of an averaged brain generated from T2w scans of the rats used in this study. The overlapping size and site of the photothrombotic lesion is displayed by a heat map on the right hemisphere. The sections are superimposed on the corresponding atlas template.[18] The heat map color red represents a low overlapping of 10%, whereas yellow indicates an overlapping of 100%. Within the M1, overlapping of the lesions is almost 100%. Cg1=cingulate cortex, area 1; Cg2=cingulate cortex, area 2; FrA=frontal association cortex; MPtA=medial parietal association cortex; PrL=prelimbic cortex; S1BF 5 primary somatosensory cortex, barrel field; S1DZ=primary somatosensory cortex, dysgranular zone; S1FL=primary somatosensory cortex, forelimb region; S1HL=primary somatosensory cortex, hind limb region; S1J=primary somatosensory cortex, jaw region; S1Tr=primary somatosensory cortex, trunk region; S1ULp=primary somatosensory cortex, upper lip region; V2ML=secondary visual cortex, mediolateral.

FIG. 2a-b: Verification of electrode placements. Consecutive brain sections encompassing the electrode site were used for fluorescent in situ hybridization to visualize choline acetyl-transferase (ChAT)+neurons of the pedunculopontine tegmental area (PTg) and c-Fos+ neurons indicating the stimulation site. Both ChAT+ and c-Fos+ cell groups as well as the electrode site (dots) were mapped onto atlas drawings of the rat brain. The relationship of electrode sites to cholinergic neurons of the PTg (A) and to the c-Fos+ neurons (B) are visualized by cloud diagrams. It is of note that ChAT+ neurons rarely expressed c-Fos in our study. The numbers below the drawings indicate the anterior-posterior distance to the bregma. The light gray areas indicate the PTg, the dark gray areas the cuneiform nucleus (Cn).

FIG. 3a-c: Assessment of locomotor behavior before and after photothrombotic stroke without and during high frequency stimulation of the mesencephalic locomotor region (MLR-HFS; day 4 after intervention). (A) Whereas no locomotion was seen after photothrombotic stroke (PT) without MLR-HFS, gait velocity changed after stroke almost to the baseline values when animals were stimulated in the MLR-HFS. *p<0.001 (95% confidence interval [CI]=20.31-24.66), #p<0.001 (95% CI=−22.82 to −16.48); ns=not significant (p>0.05, 95% CI=−0.72 to 6.40); error bars indicate standard deviation; 2-tailed paired t-test. (B) Beam-walking score, assessed according to a 7-point scale (see Materials and Methods section). After photothrombotic stroke, MLR-HFS restored gait coordination and balance significantly compared to the test condition without MLR-HFS. *p<0.001 (95% CI=5.25-6.36); #p<0.001 (95% CI=−6.38 to −3.49); ns=not significant (p>0.05, 95% CI=−0.33 to −2.06); error bars indicate standard deviation; 2-tailed paired t-test. (C) Effect of MLR-HFS on affected forepaw and hind paw. Whereas there was no difference between forepaw and hind paw regarding faults before photothrombotic stroke, rats made significantly more faults with the hind paw than with the forepaw after photothrombotic stroke even during MLR-HFS. *p=0.037 (95% CI=−2.54 to −0.13); ns, not significant (p>0.05, 95% CI=−0.29 to 0.29); error bars indicate standard deviation; 2-tailed paired t-test. FL=forelimb; HL 5 hind limb; non-slim=assessment after PT, no MLR-HFS; stim=assessment after PT, with MLR-HFS.

LIST OF TABLES

Table 1: Comparison of Gait Parameters Using the Cat-Walk System: Changes in Locomotor Variables Measured Before and After Photothrombotic Stroke Table 2: Comparison of Gait Parameters Using the Cat-Walk System: After Photothrombosis without and with Mesencephalic Locomotor Region High-Frequency Stimulation Table 3: Comparison of Gait Parameters Using the Cat-Walk System: Before Photothrombosis and Thereafter, When Mesencephalic Locomotor Region High-Frequency Stimulation Was Applied Supplemental Table S1: Individual Numeric Values for Each Gait Parameters and Paw

DESCRIPTION OF THE INVENTION

Definitions

It is to be understood that this invention is not limited to the particular methodology, protocols, cell lines, animal species, model or genera, and reagents described, as such may vary. It is also to be understood that the terminology used herein is for the purpose of describing particular embodiments only, and is not intended to limit the scope of the present invention, which will be limited only by the appended claims. For anatomical or function structures or locations of such structures or positions relative to such structures described for one species, it is to be understood that equivalent structures in other species are within the scope of the present invention.

As used herein, the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Other than in the operating examples, or where otherwise indicated, all numbers expressing quantities of time, distance, impedance, pulse lengths, current intensity, electrical stimulation or reaction conditions used herein should be understood as modified in all instances by the term "about." The term "about" can mean a range of ±1-10%.

The term "near" in referring to placement of an electrode with respect to an anatomical structure, such as "near the brainstem" or "near the cuneiform nucleus" refers to a range of electrode placement that is adjacent to the anatomical structure and may be as far as the lesser of about 1 mm or $1/100^{th}$ of the anterior-posterior length of the subject's brain.

In addition, the term "close" in referring to placement of an electrode with respect to the MLR, such as "close to the MLR," refers to an electrode placement in the vicinity and possibly within, e.g., the MLR, such that following implantation and use in DBS, improves locomotor movement in a subject with impaired mobility. In one embodiment, "close" may be as far as the lesser of about 1 mm or $1/100^{th}$ of the anterior-posterior length of the subject's brain.

As used herein, the terms "comprising" or "comprises" is intended to mean that the methods and kits of the invention include the recited steps or elements, but not excluding others. "Consisting of" shall mean excluding more than minor components and substantial method steps. Embodiments defined by each of these transition terms are within the scope of the present disclosure.

As used herein, "treating" means using a therapy to ameliorate a disease or disorder relating to impaired mobility associated with or as a result of a brain lesion or one or more of the biological manifestations of the disease or disorder; to directly or indirectly interfere with (a) one or more points in the biological cascade that leads to, or is responsible for, the disease or disorder or (b) one or more of the biological manifestations of the disease or disorder; to alleviate one or more of the symptoms, effects or side effects associated with the disease or disorder or one or more of the symptoms or disorder or treatment thereof; or to slow the progression of the disease or disorder or one or more of the biological manifestations of the disease or disorder. Treatment includes eliciting a clinically significant response. Treatment may also include improving quality of life for a subject afflicted with the disease or disorder. Throughout the specification, methods for suitable treatment of impaired mobility associated with or as a result of a brain lesion for subjects in need thereof.

As used herein, the terms "inhibit," "reverse" or "reduce" when used in the context of the invention means partial or full inhibition, reversal or reduction. It can also mean improvement.

As used herein, the term "mesencephalic locomotor region" (also referred to herein as "MLR") is a functionally—and less well—anatomically defined area of the brainstem that is associated with the initiation and control of locomotor movements in vertebrate species. The MLR is located in the mesencephalon (or midbrain), and overlaps with a region ventrolateral to the pedunculopontine tegmental nucleus, the cuneiform nucleus as well as the mesencephalic reticular nucleus.[18,19,36]

As used herein, "stimulation of mesencephalic locomotor region (MLR)" includes stimulation of MLR and/or surrounding areas such as the mesencephalic reticular (isthmic) nucleus/formation, the pre-cuneiform nucleus or latero-dorsal tegmental nucleus. Stimulation of MLR may be effected by electrical, pharmacological or optogenetic stimulus. In an embodiment, stimulation of MLR at a suitable amount or level is an amount or level sufficient to treat or reduce impaired mobility associated with a brain lesion. In another embodiment, stimulation of MLR is deep brain stimulation of the MLR. In yet another embodiment, stimulation of MLR is deep brain stimulation of the MLR as the only target to treat or reduce impaired mobility. In a further embodiment, stimulation of MLR is deep brain stimulation of the MLR performed in the absence of Parkinson's Disease. In yet a further embodiment, stimulation of MLR is deep brain stimulation of MLR performed in the absence of levodopa therapy. In an additional embodiment, stimulation of MLR is deep brain stimulation of MLR performed in the absence of internal globus pallidus (GPi) deep brain stimulation. In another additional embodiment, stimulation of MLR is deep brain stimulation of MLR performed in the absence of subthalamic nucleus (STN) deep brain stimulation. In a further additional embodiment, stimulation of MLR is deep brain stimulation of MLR performed in the absence of either internal globus pallidus (GPi) deep brain stimulation or subthalamic nucleus (STN) deep brain stimulation. In an embodiment, stimulation of the MLR is deep brain stimulation of the MLR using a high or low frequency electrical pulse. In another embodiment, stimulation of the MLR is deep brain stimulation of the MLR using a low frequency electrical pulse. In a preferred embodiment, stimulation of the MLR is deep brain stimulation of the MLR using a high frequency electrical pulse. In an embodiment, stimulation of the MLR is unilateral or bilateral deep brain stimulation. In another embodiment, stimulation of the MLR is bilateral deep brain stimulation. In a preferred embodiment, stimulation of the MLR is unilateral deep brain stimulation. In a further preferred embodiment, stimulation of the MLR is deep brain stimulation of the MLR using a high or low frequency electrical pulse ipsi lateral, contralateral or bilateral to the brain lesion. In a further preferred embodiment, stimulation of the MLR includes the DBS of the dorsal part of the MLR. In yet a further preferred embodiment, stimulation of the MLR is the DBS of only the dorsal part of the MLR (electrodes are not placed in or near any other location of the MLR that would stimulate, e.g., the ventral portion of the MLR). For example, in one embodiment, the method provides avoiding placing the electrodes at or near the ventral portion of the MLR. In terms of anatomical location, in one embodiment, stimulation of the MLR is DBS of the cuneiform or pedunculopontine tegmental nucleus. Behavior tests, such as the beam walking test, CatWalk analysis or cylinder test can be used to examine locomotion regardless of the underlying cause affecting locomotion in the subject (i.e., photothrombotic stroke, Parkinson's disease, spinal cord disease). In humans, gait, one aspect of locomotion, may be analyzed by kinematics, kinetics and/or electromyography (EMG). In an embodiment, stimulation of the MLR treats, reduces or reverses gait impairment associated with a brain lesion in a subject by improving kinematics, kinetics and/or electromyography (EMG) score of the subject. In an embodiment of the invention, the treatment, reduction or reversal of gait impairment associated with a brain lesion in a subject does not involve treatment, reduction or reversal of (1) small shuffling steps and (2) a slowness of movement with reduced stride length and walking speed as observed typically in Parkinson's Disease patients.

As used herein, the term "brain lesion" refers to an area of injury or disease within the brain. A brain lesion may be caused by a stroke, traumatic brain injury (TBI), inflammation or focal brain damage. In one embodiment, the brain lesion is in the cortex. In another embodiment, the brain lesion is in the midbrain but not in the substantia nigra pars compacta. In a separate embodiment, the brain lesion may be in the midbrain but not in one or more anatomical structures associated with Parkinson's Disease or Parkinsonism. In another embodiment, the brain lesion is not in the midbrain.

As used herein, the term "traumatic brain injury" (TBI) refers to a non-disease event commonly caused by an injury resulting in an insult to the brain. TBI may be caused, for example, by impact forces, in which the head strikes or is struck by something, or impulsive forces, in which the head moves without itself being subject to blunt trauma (for example, when the chest hits something and the head snaps forward; or as a result of rapid acceleration or deceleration of the head). TBI commonly results, for example, from a sports-related injury, a motor vehicle accident, an accidental fall, or an assault.

As used herein, the term "brain damage" refers to conditions affecting a subject's brain where the brain structure and/or biochemical composition is altered. Alteration in brain structure and/or biochemical composition may be due to interruption or reduction in blood supply to part of the brain, such as in stroke, depriving brain tissue of oxygen and nutrients and death of brain cells. Brain damage also includes "brain injury" which refers to physical injuries to a subject's brain where the brain structure is altered, for example by: disruption of neuronal cell bodies; hemorrhage; diffuse axonal injuries accompanied by increased beta-amyloid and plaques and rearrangement of axonal structure within the brain tissue; and hydrocephalus. Examples of brain injury include, but are not limited to, diffuse or mild traumatic brain injury (TBI), Multi-Infarct Dementia (MID) (also known as "vascular dementia") and subdural hematoma.

As used herein, the term "focal brain damage" may refer to brain damage at a specific location.

As used herein, "stroke" is a cerebrovascular disorder due to insufficiency of arterial blow in the brain. "Stroke" may be classified as ischemic stroke or hemorrhagic stroke. Ischemic stroke is caused by a blood clot that blocks or plugs a blood vessel in the brain; whereas, hemorrhagic stroke is caused by a blood vessel that breaks and bleeds in the brain. Symptoms of stroke include, but are not limited to, sudden numbness or weakness of the face, arm or leg, especially on one side of the body, sudden confusion, trouble speaking or understanding speech, sudden trouble seeing in one or both eyes, sudden trouble walking, dizziness, loss of balance or coordination, and sudden severe headache with no known cause. Motor symptoms after stroke (such as impairment of gait and balance, affecting around about 80% of stroke survivors) may be expected if at least one of the following cerebral structures involved in motor function are affected: cerebral motor cortex, supplementary motor area, corticospinal tract (e.g. within the internal capsule, corona radiate or brainstem), or cerebellum. Gait impairment after stroke may be characterized by a slow and asymmetrical walking pattern with reduced stride length and a prolonged swing phase of the affected limb (hemiplegic gait pattern). In the long-term, post-stroke spasticity may occur and further impair walking. Of note, gait impairment after stroke varies with stroke severity, location of infarction and other individual differences. In order to characterize gait impairment after stroke observational gait analyses are most often used. Stroke may result in paralysis of one side of the body (hemiplegia) or slight paralysis or weakness on one side of the body (hemiparesis). Damage to brain tissue due to stroke include brain cell death. In order to characterize better pathophysiology and motor impairment after stroke, different animal models in rodents, cats, pigs and non-human primates have been introduced. Most common models are the photothrombotic stroke model, the transient or permanent middle cerebral artery occlusion (MCAo) model, the embolic stroke model and the endothelin-I model. Other models are well known and contemplated for use with the invention. There are different methods to assess/analyze after induction of experimental stroke, e.g., the CatWalk analysis, ladder rung walking test or beam walking test.

As used herein, the term "continuous electrical stimulation" may include an uninterrupted stimulation of a distinct brain area by a stimulating electrode in a subject, for about 24 hours a day, at least one day up to, e.g., 30 days or beyond, as needed. For example, in animals, a suitable amount or level of "continuous electrical stimulation" may be anywhere from one day to 60 days. In another example, in humans, a suitable amount or level of "continuous electrical stimulation" may be anywhere from one day to an indefinite duration, as needed. The duration of "continuous electrical stimulation" may be dependent on the subject's responsiveness and, in some cases, any beneficial latent or prolonged/lasting effect of the stimulation following e.g., its cessation or interruption on the subject.

As used herein, the term "high frequency electrical stimulation" refers to a frequency of about 100 Hz or higher. Typically, a suitable amount or level of applied high frequency stimulation in a subject may range between about 100 Hz to 130 Hz.

The term "low frequency electrical stimulation" refers to a frequency below about 100 Hz. For example, a suitable amount or level of applied low frequency stimulation in a subject may range between about 25 and 50 Hz.

As used herein, the term "square wave pulse" refers to a non-sinusoidal periodic wave form in which the amplitude alternates at a steady frequency between fixed minimum and maximum values with the same minimum and maximum. The term "monophasic square wave pulse" refers to a square wave pulse whose amplitude is oscillating only between about 0 and +1. The term "biphasic square wave pulse" refers to a square wave pulse whose amplitude undulates between about −1 and +1 with regard to the zero axis. The values may be normalized.

As used herein, the term "triangular wave pulse" refers to a periodic triangular shaped waveform but fulfills otherwise the definition of a square wave pulse.

As used herein, the term "sinusoidal pulse wave" refers to a continuous wave with a smooth-curved shape oscillating around the zero axis. Mathematically, a sine function underlies this wave form.

As used herein, the term "inability to walk" refers to a response indicating that an individual is or was unable to walk.

As used herein, the term "loss of balance" or "postural instability" refers to a tendency to fall or the inability to keep oneself from falling; imbalance.

METHODS OF THE INVENTION

The invention provides methods of treating impaired mobility associated with a brain lesion in a subject. In one embodiment, the method comprises stimulation of mesencephalic locomotor region (MLR) of the subject at a suitable amount or level so as to reverse impaired mobility in the subject, thereby treating impaired mobility associated with a brain lesion in the subject. Examples of impaired mobility include, but are not limited to, inability to walk, loss of balance and gait impairment, or a combination thereof.

In accordance with the practice of the invention, gait impairment may comprise any of decreased walking velocity, asymmetric walking pattern, decreased stride length, increased stride width, prolonged swing phase of affected limb, diminished ability to negotiate physical obstacle, diminished ability to adjust walking to changes in terrain, loss of rhythmic movement, diminished ability to move across a beam or ladder and a combination thereof.

The causes of the brain lesion may include any of a stroke, traumatic brain injury (TBI), inflammation or focal brain damage. Merely by way of example, the brain lesion may be caused by an ischemic stroke, hemorrhagic stroke, photothrombotic stroke, traumatic brain injury (TBI), inflammatory or any other source of focal brain damage. In one embodiment, the brain lesion may be caused by an ischemic stroke, hemorrhagic stroke, photothrombotic stroke, traumatic brain injury (TBI), inflammatory or any other source of focal brain damage but not Parkinson's Disease.

In an embodiment of the invention, the brain lesion is not degeneration of the neuromelanin-containing neurons in the brainstem, particularly those in the pars compacta of the substantia nigra. In an embodiment, the brain lesion does not result in dopamine deficit. In an embodiment, the brain lesion is independent or does not involve the dopamine pathway in the substantia nigra. In an embodiment, the brain lesion is not associated with Parkinson's Disease. In an embodiment, the brain lesion does not produce symptoms of tremor or dystonia associated with Parkinson's Disease.

In one embodiment, the brain lesion may be located at or about the sensorimotor cortex of the subject's brain or its outflow fiber pathways. Merely by way of example, the sensorimotor cortex of the subject's brain is or may include any one or more of primary motor cortex, premotor cortex, supplementary motor area (SMA), posterior parietal cortex, primary somatosensory cortex and/or equivalents thereof. In another embodiment, the sensorimotor cortex of the subject's brain includes the primary motor cortex, secondary motor cortex, and primary somatosensory cortex, and equivalents thereof.

In another embodiment of the invention, the brain lesion may be located outside of a sensorimotor cortex of the subject's brain. For example, when the brain lesion is located outside of the sensorimotor cortex of the subject's brain, the lesion may be located in one or more of a cerebellum, basal ganglia, subcortical motor nuclei and equivalents thereof.

In another embodiment of the invention, the brain lesion may be located at the cerebral motor cortex, supplementary motor area, corticospinal tract (e.g. within the internal capsule, corona radiate or brainstem) and/or cerebellum and equivalents thereof.

In a further embodiment, the brain lesion may be located in any of the left hemisphere of the subject's brain, right hemisphere of the subject's brain or both hemispheres of the subject's brain.

In specific embodiments of the invention, the brain lesion occurs at a site in the brain which causes impaired mobility. In one embodiment, a site in the brain which causes impaired mobility may affect the motor function of the cerebral motor cortex, supplementary motor area, corticospinal tract (e.g. within the internal capsule, corona radiate or brainstem) or cerebellum and/or equivalent thereof.

Merely by way of example, the stimulation of mesencephalic locomotor region (MLR) may involve neuronal activation by any of the following means, including but are not limited to, an electrical, pharmacological or optogenetic stimulation. Neuronal activation may include antidromic impulse and/or orthodromic impulse. Without being bound by any theory, in an embodiment of the invention, stimulation of the MLR may shield the mesencephalic and downstream locomotor systems from aberrant cortical input after stroke and allows for autonomous function of these circuits, so as to reduce or reverse impaired mobility associated with a brain lesion, wherein the brain lesion is in the cortex. In one embodiment, the electrical stimulation is deep brain stimulation. In one embodiment, stimulation of the MLR may be achieved with an electrode in a monopolar configuration. In another embodiment, stimulation of the MLR may be achieved with bipolar electrodes (see Herrington, T. M. el al. (2016) Mechanisms of deep brain stimulation. *J. Neurophysiol.* 115(1): 19-38 for a discussion of a DBS system as well as placement of electrode and pulse generator (also referred to as stimulus generator) on electric field, and a discussion on electrostimulation conditions). In another embodiment, the stimulus generator may be implanted. In a separate embodiment, stimulation of the MLR may be achieved with a directional electrode (using merely as an example, Boston Scientific's DB-2202-30 or DB-2202-45). In another embodiment, stimulation of the MLR may be achieved with one or more electrodes designed to create a desired electric field configuration. In a different embodiment, stimulation of the MLR may be achieved with one or more electrodes designed for monophasic, biphasic or multiphasic modes.

In accordance with the practice of the invention, the electrical stimulation may comprise a pulse shape. Examples of pulse shapes include a monophasic square wave pulse, biphasic square wave pulse, triangular pulse and/or sinusoidal pulse.

In another embodiment of the method, a suitable amount or level of the electrical stimulation may comprise one or more pulse lengths including those selected from about 10 to 500 microseconds. In a specific embodiment, a suitable amount or level of the pulse length may be about 60 microseconds. In an additional embodiment, a suitable amount or level of the pulse length may be a value between about 50 to 20 microseconds. In yet another embodiment, a suitable amount or level of the pulse length may be a value between about 100 to 300 microseconds.

Further, the electrical stimulation may comprise low or high-frequency stimulation. For example, a suitable amount or level of the electrical stimulation may comprise one or more frequencies from a range of about 10 to 175 Hz; more specifically, a range of about 10 to 15 Hz, 15 to 20 Hz; 20 to 30 Hz; 40 to 50 Hz; 50 to 60 Hz, 70 to 80 Hz; 80 to 90 Hz; 90 to 100 Hz; 100 to 125 Hz, 125 to 150 Hz; 150 to 175 Hz. Merely by way of example, the high-frequency stimulation may be a value between a range of about 130 to 175 Hz, inclusive. In another embodiment of the method, the low-frequency stimulation may be a value between about 10 to 60 Hz, inclusive.

In an embodiment, the pulse length is adjusted so as to be effective at treating, inhibiting or reversing impaired mobility. In another embodiment, the frequency of the electrical stimulation is adjusted so as to be effective at treating, inhibiting or reversing impaired mobility. In another embodiment, the pulse length and frequency of the electrical stimulation are adjusted so as to be effective at treating, inhibiting, reducing or reversing impaired mobility.

In a particular embodiment of the method, the high-frequency stimulation comprises a combination of a frequency of about 130 Hz, monophasic square wave pulses and a pulse length of about 60 microseconds.

Further, merely as an example, the electrical stimulation may comprise a stimulus generator (also referred to as a pulse generator) such as STG 4002 or 4004 (Multichannel Systems, Reutlingen, Germany) or equivalent. The stimulus generator, e.g., STG 4002 or 4004 or equivalent, may comprise a voltage compliance range of about 120V. In an embodiment, the stimulus generator may be powered by a rechargeable or non-rechargeable battery. In another embodiment of the method, the stimulus generator may comprise a constant current stimulation as a feature thereby, e.g., to permit adjustment of voltage with changes in tissue impedance so as to provide constant current output at the electrode. For example, the electrode may comprise platinum and/or iridium. In one embodiment of the invention, the electrode comprises a monopolar microelectrode. In one embodiment, the electrode comprises a directional microelectrode (e.g., a lead kit model no. DB-2202-30 or DB2202-45 (Boston Scientific (Marlborough, Mass.)). In another embodiment, DBS may be performed using a DBS system comprising an implantable electrode, an implantable pulse generator and an energy source, such as either a rechargeable battery or a non-rechargeable battery (for example, see Herrington, T. M. et al. (2016) Mechanisms of deep brain stimulation. *J. Neurophysiol.* 115(1): 19-38 for a discussion of a DBS system as well as placement of electrode and pulse generator on electric field, and a discussion on electrostimulation conditions). Suitable examples of implantable leads and implantable pulse generators include, but are not limited to, Activa PC Stimulator (model no. 37601) and Activa RC Stimulator (model no 37612) with both pulse generators compatible with lead (i.e., stimulating electrode) model no. 3387 and model no. 3389 and Activa PC Stimulator pulse generator compatible with lead model no. 3391 (Medronic (Minneapolis, Minn.)) and Vercise™ PC DBS system (implantable pulse generator model no. DB-1140 used in combination with lead kit, such as, model no. DB-2201-30DC, model no. DB-2201-45DC, model no. DB-2202-30 and/or model no. DB-2202-45) (Boston Scientific (Marlborough, Mass.)).

In accordance with the practice of the invention, the electrode may be implanted at or about the mesencephalic locomotor region (MLR). For example, the electrode may be implanted at or about the MLR ipsilateral to the brain lesion. The MLR may comprise any of pedunculopontine nucleus, cuneiform nucleus, midbrain extrapyramidal area and equivalence thereof. In a further embodiment, the MLR comprises noncholinergic, predominantly glutamatergic cells localized in the lateral pontine tegmentum, which form a strip extending from ventrolateral periaqueductal gray matter to a region ventromedial to pedunculopontine tegmental nucleus with ipsilateral predominance or equivalent thereof.

In yet another embodiment of the method, the electrode may be implanted at or about the cuneiform nucleus. In a further embodiment, the electrode is implanted near the brain stem.

In another embodiment of the invention, the electrical stimulation comprises a current threshold for stimulating locomotion. For example, the current threshold for stimulating locomotion may be the lowest current intensity for evoking locomotion. In yet another embodiment, the lowest current intensity evoking locomotion may be a value between about 20 µA to 5 mA. For example, the lowest current intensity evoking locomotion may be a value between about 20 to 60 µA (e.g., for small mammals such a rodent). In an additional embodiment, the lowest current intensity evoking locomotion may be a value between about 30 to 40 µA. In yet another embodiment, the lowest current intensity evoking locomotion may be a value between about 25 to 50 µA. In yet a further embodiment, the lowest current intensity evoking locomotion may be a value between about 0.5 to 5 mA (e.g., for larger mammals such as a human). It is understood to those skilled in the art that other values may be applicable depending on the size and type of mammal.

Further, in one embodiment of the invention, the electrode may have a mean impedance of about 0.8 to 1.2 MΩ (e.g. for smaller mammals such a rodent). In an additional embodiment, the electrode may have a mean impedance of about 0.5 to 1.5 MΩ. In yet another embodiment of the method, the electrode may have a mean impedance of about 300 to 5000Ω (e.g., for larger mammals such as humans). It is understood to those skilled in the art that other values for mean impedance may be applicable depending on the size and type of mammal.

Examples of suitable subjects include, but are not limited to, a human, monkey, chimpanzee, ape, lemur, mouse, rat, squirrel, guinea pig, hamster, rabbit, shrew, mole, mink, cat, dog, pig, cow, goat, donkey, horse, sheep, and non-human primate. In a preferred embodiment, the subject is a human.

In another embodiment of the method, reversing the impaired mobility in the subject comprises any of greater walking velocity, an increase in symmetric walking pattern, greater stride length, decreased stride width, reduced duration of swing phase of affected limb, greater ability to negotiate physical obstacle, greater ability to adjust walking to changes in terrain, increased rhythmic movement, greater ability to move across a beam or ladder and a combination thereof.

In another embodiment of the method, the pharmacological stimulation comprises administering a pharmacologic agent which stimulates or modulates cells of the MLR.

In another embodiment of the method, the pharmacologic agent is selected from the group consisting of muscarinic cholinergic antagonists.

The invention provides a method of inhibiting a motor deficit in a subject after a stroke. In one embodiment, the method comprises administering continuous electrical stimulation to the mesencephalic locomotor region (MLR) of the subject under sufficient conditions so as to inhibit the motor deficit of the subject.

The invention provides a method of reducing a motor deficit in a subject after a stroke. In one embodiment, the method comprises administering continuous electrical stimulation to the mesencephalic locomotor region (MLR) of the subject under sufficient conditions so as to reduce the motor deficit of the subject. In one embodiment, the method comprises administering continuous electrical stimulation to the mesencephalic locomotor region (MLR) of the subject under sufficient conditions so as to improve the motor function of the subject, thereby reducing the motor deficit of the subject.

The invention further provides a method of treating a motor deficit of a subject after a stroke. In one embodiment, the method comprises administering continuous electrical stimulation to the MLR of the subject in a suitable amount or level so as to inhibit, reverse or reduce the motor deficit of the subject.

The invention additionally provides a method of treating a rehabilitating subject suffering from a motor deficit as a result of a stroke by inhibiting, reducing or reversing the motor deficit(s) of the subject. The motor deficit may include, but is not limited to, a gait impairment, inability to walk, or loss of balance or combination thereof. The method comprises administering continuous electrical stimulation to the mesencephalic locomotor region (MLR) of the subject under sufficient conditions so as to inhibit, reduce or reverse the motor deficit. In one embodiment electrical stimulation to the MLR involves electrical stimulation of the dorsal portion of the MLR. In another embodiment, electrical stimulation to the MLR involves electrical stimulation of the dorsal portion of the MLR but not to the ventral portion of the MLR. In yet a further embodiment, electrical stimulation to the MLR involves electrical stimulation of the dorsal and ventral portions of the MLR.

In one embodiment of the invention, the continuous electrical stimulation may be applied to the MLR in a suitable amount or level so as to stimulate the mesencephalic and spinal central pattern generators (CPGs) or shield the mesencephalic and spinal CPGs from aberrant cortical input.

In one embodiment, the shielding of the mesencephalic and spinal CPGs from aberrant cortical input permits autonomous function of locomotor circuits comprising mesencephalic and spinal CPGs. In accordance with the practice of the invention, the MLR may be at or near the brainstem of the subject. In another embodiment, the MLR may be located in the mesencephalon, ventral to the inferior colliculus and near the cuneiform nucleus. In yet a further embodiment, the MLR comprises noncholinergic, predominantly glutamatergic cells localized in the lateral pontine tegmentum, which form a strip extending from ventrolateral periaqueductal gray matter to a region ventromedial to pedunculopontine tegmental nucleus with ipsilateral predominance or equivalent thereof.

In accordance with the practice of the invention, continuous electrical stimulation to the MLR may comprise implantation of the electrode near or close to the MLR. In one embodiment, the electrode is implanted slightly above the dorsal part of the MLR. For example, the electrode may be implanted at a coordinate of about 7.8 mm posterior, 2.0 mm lateral and 5.8 mm ventral to the bregma of a small mammal, such as a rat or equivalent thereof. It is understood to those skilled in the art that other coordinate values may be applicable depending on the size and type of the subject.

In one embodiment, the tip of the electrode may be placed ipsilateral to the brain lesion associated with the stroke. In another embodiment, continuous electrical stimulation to the MLR comprises implantation of electrode ipsilateral to site of the brain lesion associated with the stroke.

In one embodiment, the brain lesion is in the cortex. In another embodiment, the cortical brain lesion is a cortical lesion in any of, but not limited to, cingulate cortex area 1, cingulate cortex area 2, frontal association cortex, medial parietal association cortex, prelimbic cortex, primary somatosensory cortex, primary motor cortex and secondary motor cortex or functionally equivalent anatomical structure. In another embodiment, the brain lesion may be in the cerebral motor cortex, supplementary motor area, corticospinal tract (e.g. within the internal capsule, corona radiate or brainstem) and/or cerebellum and/or equivalents thereof. In another embodiment, the brain lesion may affect the function of cerebral motor cortex, supplementary motor area, corticospinal tract (e.g. within the internal capsule, corona radiate or brainstem) and/or cerebellum and/or equivalents thereof. In one embodiment, the brain lesion does not involve (or does not substantially involve) nigro-striatal dopaminergic neuronal cell death. In one embodiment, the brain lesion is not a lesion caused by abnormal accumulation and aggregation of alpha-synuclein to form Lewy bodies in neurons. In one embodiment, the brain lesion is not a lesion caused by Lewy bodies developing in the substantia nigra, midbrain, neocortex and/or basal forebrain and death of the associated neurons. In one embodiment, the brain lesion does not affect more than 70% of dopaminergic neurons in the substantia nigra pars compacta so as to produce motor symptoms, such as bradykinesia rigidity, tremor at rest and postural instability.

The invention also provides a method of determining therapeutic efficacy of deep brain stimulation in restoring gait in an animal subject after experimentally induced stroke. In one embodiment, the method comprises: a) implantation of electrode ipsilateral or both, ipsilateral and contralateral to the stroke at mesencephalic locomotor region; b) administration of electrical stimulation; c) observation of locomotor behavior before and after electrical stimulation; d) comparison of observed locomotor behavior before and after electrical stimulation to determine if electrical stimulation increases and/or improves locomotor behavior.

In another embodiment of the method, the brain lesion may be induced by administering a photo reactive label and light activation of the label. Examples of the photoreactive label include, but are not limited to, Rose Bengal, erythrosine B or sodium fluorescein. In a preferred embodiment of the method, the photo reactive label is Rose Bengal. In an embodiment, the brain lesion may be induced experimentally. In another embodiment, the brain lesion may occur by natural causes.

In another embodiment of the method, the light is delivered using a light guide. In another embodiment of the method, the light is delivered to an area corresponding to sensorimotor cortex of the subject's brain.

In one embodiment of the invention, the electrical stimulation comprises high-frequency stimulation. In one embodiment of the invention, the electrical stimulation comprises low-frequency stimulation. In one embodiment of the invention, the electrical stimulation comprises a combination of high-frequency and low-frequency stimulation. Additionally, in another embodiment, the electrical stimulation comprises monophasic square wave pulses.

In another embodiment of the method, the experimentally induced stroke comprises localized light activation of a photo reactive label at or about any of primary motor cortex, secondary motor cortex, primary somatosensory cortex of forelimb, primary somatosensory cortex of hind limb and combination thereof. Examples of the photo reactive label include, but are not limited to, Rose Bengal.

Locomotor behavior tests include, but are not limited to, beam-walking test, ladder rung walking test and CatWalk system test (Noldus, Wageningen, the Netherlands).

KITS OF THE INVENTION

According to another aspect of the invention, kits are provided.

The invention provides a kit for treating impaired mobility associated with a brain lesion in a subject. In one embodiment, the kit comprises an electrode for administering electrical stimulation at mesencephalic locomotor region of the subject, and a label and instructions on how to use the kit for treating impaired mobility associated with a brain lesion in a subject as described herein. The subject may be a mammal such as, but no limited to, human, monkey, chimpanzee, ape, lemur, mouse, rat, squirrel, guinea pig, hamster, rabbit, shrew, mole, mink, cat, dog, pig, cow, goat, donkey, horse, sheep, and non-human primate.

In one embodiment, the kit comprises an electrode which is a monopolar microelectrode. For example, the electrode may permit high-frequency stimulation of the MLR. In another embodiment, the electrode may comprise or contain platinum and/or iridium. Additionally, in a further embodiment, the electrode may have an impedance of about 0.8-1.2 M$\Omega$ (for use in small mammals) or a mean impedance of about 0.3-5$\Omega$ (for use in larger mammals such as humans). In yet a further embodiment, the electrode may have a mean impedance of about 0.5-1.5 M$\Omega$ (e.g., for use in small mammals such as, e.g., rodents). In a specific embodiment, the electrode is a MLR-HFS (catalog # UE-PSEGSECN1M; FHC, Bowdoin, Me.) or equivalent thereof. Suitable examples of electrodes include, but are not limited to, lead model number 3387, 3389 or 3391 (Medtronic (Minneapolis, Minn.)) or equivalent thereof; or DB-2201-30DC or DB-2201-45DC (Medtronic (Minneapolis, Minn.)). In addition, electrodes designed to generate specific electric field configurations are contemplated as well as electrodes which may be used in monophasic, biphasic or multiphasic modes.

In one embodiment, the kit comprises an electrode which is a directional microelectrode. In an embodiment, the electrode may comprise or contain platinum and/or iridium. Suitable examples of electrodes include, but are not limited to, DB-2202-30 or DB-2202-45 (Boston Scientific (Marlborough, Mass.)) or equivalent thereof.

In accordance with the practice of the invention, the kit may further comprise an electrical stimulus generator. The electrical stimulus generator may provide a constant current output and/or a constant voltage output. In another embodiment, the electrical stimulus generator may adjust voltage to changes in tissue impedance so as to provide constant current output at the electrode. Merely by way of example, the electrical stimulus generator may produce electrical stimulation comprising one or more frequencies selected from about 10 to 175 Hz. In an additional embodiment, the electrical stimulation corresponding to high-frequency stimulation may be a value between about 130 to 175 Hz, inclusive.

In a further embodiment, the electrical stimulus generator may produce an electrical pulse shape selected from the group consisting of a monophasic square wave pulse, biphasic square wave pulse, triangular pulse and sinusoidal pulse. Merely by way of example, the electrical stimulus generator may produce an electrical pulse with a pulse length selected from about 10 to 500 microseconds. In a specific embodiment, the electrical stimulus generator is STG 4002 or 4004 (Multichannel Systems, Reutlingen, Germany) or equivalent thereof.

Additionally, the kit may further comprise screws for affixing the electrode to skull of the subject. In one embodiment, the screws may be stainless steel or plastic screws.

Also, the kit may further comprise an adhesive filler for affixing the electrode to skull of the subject. In one embodiment, the adhesive filler comprises dental cement.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Animals

All experiments were performed in adult (250-275 g, 6-8 weeks old) male Wistar rats (n=20; Charles River, Sulzfeld, Germany). Rats were acclimatized for one week in an animal facility and housed in a room with controlled temperature (22±0.5° C.) under a 12 h/12 h light/dark cycle. They were allowed free access to food and water. All animal experiments were approved by the institutional review board of Julius-Maximilians-University, Würzburg and by the local authorities of lower Frankonia (Regierung von Unterfranken, Würzburg, Germany).

Induction of Photothrombotic Stroke

Animals were divided into 2 groups: the first underwent photothrombotic stroke only (n=10), whereas the second was subjected to both photothrombosis and electrode insertion into the MLR (n=10, see below), to exclude any behavioral effect of electrode implantation into the MLR.

Rats were anesthetized with 2.5% isoflurane during the surgery. Body temperature was maintained at 37±0.5° C. by a feedback-controlled heating system. A photothrombotic cerebral stroke was induced in all rats as follows:[20] a template with an aperture (10×5 mm) for the light source was put on the exposed skull 5 mm anterior to 5 mm posterior and 0.5 mm to 5.5 mm lateral to the bregma, an area which corresponds to the sensorimotor cortex (FIG. 1).[18] A light guide was placed over the aperture. 0.5 mL Rose Bengal (Sigma) in NaCl 0.9% (10 mg/mL) was administered intravenously, and the brain was illuminated (Olympus KL1500LCD) through the intact skull for 15 min. Immediately after this procedure, a microelectrode was implanted in half of the animals (see section below).

Microelectrode Implantation

For high-frequency stimulation of the MLR (MLR-HFS), monopolar microelectrodes (Catalogue-# UE-PSEGSECN1M; FHC Inc., Bowdoin, Me., USA) were used in this study. To avoid electrochemical neurotoxicity, electrodes made of platinum/iridium (Pt/Ir) with a mean impedance of 0.93 MΩ (range: 0.8-1.2 MΩ) were used. Electrodes were implanted close to the dorsal part of the MLR ipsilateral to the lesion (coordinates: 7.8 mm posterior, 2.0 mm lateral and 5.8 mm ventral to the bregma) as described in detail elsewhere.[21] By using the aforementioned coordinates, the tip of the electrode was placed slightly above the dorsal part of the MLR (FIG. 2A), which avoids the destruction of this small structure but still ensure an effect of stimulation on the MLR. The electrode was implanted ipsilateral to the photothrombotic stroke for the following reason: In a recent study by Bachmann et al.,[22] unilateral injection of FastBlue into the left rostral medulla oblongata resulted in predominant retrograde labeling of the left MLR and left motor cortical areas and to a lesser extent of the contralateral cortex indicating a largely uncrossed organization of the corticomesencephalic spinal locomotor circuit (as corroborated by Matsumura et al.[23] in Macaque monkey).

Five stainless steel screws (M1.6; length, 3 mm; Hummer&Rieß, Nürnberg, Germany) were inserted in boreholes without penetrating the dura overlaying the brain surface. A custom-made plug (GT-Labortechnik, Arnstein, Germany) was put on the pin of the electrode, and the ground wire of the plug was connected with one of the screws. To fix the electrode/plug with the bone screws, dental cement was applied on the skull and molded around the electrode/plug by forming a small cap. Wound edges were closed with a suture at the front and behind the cap. Thereafter, animals were allowed to wake up.

Behavioral Testing

Rats were trained for 7 days to traverse a horizontal wooden beam (90 cm long, 9 mm wide, 70 cm above ground). At the same time, they learned to cross the runway of the CatWalk system (Noldus, Wageningen, the Netherlands), a video-based analysis system to assess static and dynamic gait parameters (for a complete description of this method, see Hamers et al.[24]). On the last day of training, traversing the wooden beam and crossing the CatWalk system (3 runs per animal) were recorded; these measurements were used as baseline values. Induction of photothrombotic stroke and implantation of the electrode were performed 1 day later (i.e., on day 8 after the beginning of training). Three days after intervention, locomotor behavior was first investigated without stimulation using the CatWalk system. Three hours later, the same experiment was carried out with HFS (frequency=130 Hz, pulse length=60 microseconds, pulse shape=monophasic square wave pulses) using the stimulus generator STG 4002 (Multichannel Systems, Reutlingen, Germany). This device includes a large voltage compliance range of 120V, as well as constant current stimulation as a particular feature. In the current mode, the device is able to adjust the voltage to changes in tissue impedance, and thus provides a constant current output at the electrode. Before starting gait analyses, a threshold current intensity was determined for each animal by observing spontaneous locomotor behavior as described recently.[22] The current threshold for stimulation-evoked locomotion was determined by beginning at 20 µA and then increasing the intensity in 10 µA steps until the maximal locomotion was seen. Switching on and off the device tested reproducibility of the stimulus-induced locomotion. Thereafter, the lowest current-evoking locomotion was chosen for further testing. In the present study, the lowest current intensity resulting in increased locomotor activity was 40 µA in all tested animals. Three crossings of the CatWalk runway without interruption/hesitation were required for a valid kinematic gait analysis in each animal. Data were analyzed using the CatWalkXT 10 software.

The 5 most widely used gait parameters in recently published studies on locomotion after stroke [25,26] were analyzed, namely step cycle, swing speed, and duty cycle (i.e., dynamic paw parameters) as well as stride length and contact area (i.e., static paw parameters).

The beam-walking task was performed 4 days after photothrombosis using the same parameters for HFS as during CatWalk testing. Three traverses per animal were performed and video was recorded. The time passing between the first and the last step on the beam was taken to calculate the gait speed. Fine motor coordination and balance were further determined using a 7-point nonparametric scale and animals were scored as follows[27]: 1=unable to traverse or falls off the beam; 2=unable to traverse the beam but able to maintain balance on the beam; 3=able to traverse the beam by dragging the affected limb; 4=able to traverse the beam and—at least once—to place the affected limb on the horizontal surface of the beam; 5=the affected limbs are used in <50% of its steps on the beam; 6=able to traverse the beam by using the affected limbs (contralateral to the lesion and implanted electrode) for >50% of its steps along the beam; 7=able to traverse the beam normally with no more than 2 foot slips. To examine whether the use of the left fore- and hind-limb changes during MLR-HFS after photothrombotic stroke, paw slips and misses off the beam (1 point per fault) were counted before photothrombotic stroke and thereafter under HFS conditions. Both the CatWalk analysis and the beam-walking test were also carried out in rats subjected to photothrombotic stroke alone, to investigate whether electrode implantation into the MLR influences locomotor behavior.

Measurement of Lesion Volume

Lesion size was visualized using T2-weighted (T2w) magnetic resonance imaging (MRI) on a 3.0T scanner (MAGNETOM Trio; Siemens, Erlangen Germany). T2w scans were acquired with turbo spin-echo sequences (echo time=105 milliseconds, repetition time=2,100 milliseconds) and infarct volume was determined using ImageJ Analysis Software 1.45s (National Institutes of Health, Bethesda, Md.; http://rsb.info.nih.gov/ij/: Pascau, Javier and Perez, Jose M. M. *Image Processing with Image J*, $2^{nd}$ Edition, Birmingham: Packt Publishing, 2015. ISBN13: 9781785889837); the hyper intense lesion on each scan (1 mm thick) was traced manually and the areas were then summed and multiplied by the slice thickness.

To compare the location and size of the photothrombotic lesion among all animals, an average brain of these animals was generated and all lesions were overlapped in a color-coded heat map on this brain as follows. T2w images were brain-extracted with the brain extraction tool of FSL (FMRIB, Oxford, UK) optimized for rodent brains and additionally corrected manually. All lesions were segmented manually in original data. Rat brains were registered with FLIRT (FMRIB). The lesion masks were transformed according to the individual brain registrations. The sum of all lesions was overlaid on the normalized average brain data using a color lookup table. Thereafter, 3 brain sections representing each plane were superimposed on the corresponding atlas template.[18]

Immunohistochemistry

After deep anesthesia, rats were killed by decapitation and the brains were harvested rapidly and immediately frozen at −20° C. Coronal sections (12 µm thick) were cut using a cryostat (Leica 3050; Leica Microsystems, Wetzlar, Germany). Sections encompassing the MLR were stained with hematoxylin and eosin to visualize the anatomic locations of the electrode tip. The localization of the stimulation sites was assessed by choosing 2 approaches. First, the relationship of the electrode tip location was mapped out with respect to the cholinergic neurons of the PTg; second, c-Fos expression sites were compared to the localization of cholinergic neurons.

To identify choline acetyl-transferase (ChAT)-positive neurons of the PTg and to visualize the expression of c-Fos, fluorescent in situ hybridization of sections encompassing the MLR and lesion due to the electrode tip were performed using the RNAscope Multiplex Fluorescent v2 Assay according to the manufacturer's instructions (Advanced Cell Diagnostics, Milan, Italy; catalogue #323100). Target probes for c-Fos (RNAscope probe Rn-Fos, catalogue #403591) and ChAT (RNAscope probe Rn-Chat-C2, catalogue #430111-C2) were designed by Advanced Cell Diagnostics. After amplification and label application, sections were counterstained with 4,6-diamidino-2-phenylindole (Sigma-Aldrich, St Louis, Mo.; catalogue # D9542). Images were acquired with a Leica MDi8 microscope (magnification=40×). Finally, ChAT+ cells of the PTg as well as c-Fos+ cells around the stimulation site of each animal were delineated as a cloud onto atlas drawings of consecutive (corresponding) brain sections. These cell groups were then related to the distal end of the electrode trajectory.

Statistical Analysis

For gait speed and number of step cycles measured by the CatWalk system, individual averages of each rat were calculated over 3 runs for each time point (i.e., measurements before and after photothrombotic stroke, as well as during MLR-HFS) and used to get group means and standard deviations (SDs). Gait speed and number of step cycles were further analyzed using repeated measures analysis of variance (ANOVA) with Green-house—Geisser corrections as appropriate for sphericity violations. Post hoc analyses were performed with Tukey multiple comparison test.

Additional gait parameters (i.e., step cycle, swing speed, and duty cycle as well as stride length and contact area) measured by the CatWalk system were analyzed as raw values in relation to instantaneous body velocity.[28] This was necessary, because most gait parameters change as a function of speed[29] and photothrombotic stroke reduces gait velocity, such that the intervention itself would act as a confounder. In a first step, we plotted scattergraphs of each parameter against body velocity and compared the mostly nonlinear distributions under the 3 different treatment conditions visually. We then conducted global and velocity-restricted group comparisons (repeated measures ANOVA and post hoc t-tests for paired samples with Bonferroni correction) at slow (16-30 cm/s), medium (30-65 cm/s), and fast (65-150 cm/s) body speed.

For the beam-walking test, statistical differences of gait velocity and scores before photothrombosis and 4 days after intervention under MLR-HFS were calculated using the 2-tailed paired t-test. All values are presented as mean±SD with 95% confidence intervals (CIs). Probability values<0.05 were considered to indicate statistical significance. Statistical Package for the Social Sciences (SPSS 17.0; IBM, Armonk, N.Y.) software was used for statistical analysis.

Results

Baseline Characteristics

One animal died in each group during the experiment and thus had to be excluded from the analyses. T2w scans revealed a photothrombotic lesion in all animals encompassing the right sensorimotor cortex (see FIG. 1A, B). On T2w scans, lesion size did not differ significantly between both groups (mean lesion volume: first group, 72.8±6.4 mm$^3$ vs second group, 84.9±9.6 mm$^3$; p=0.32). To further determine size and site of the photothrombotic stroke, all scanned brains were coregistered and a template was calculated; thereafter, the degree of overlapping of the photothrombotic lesions was visualized by a color-coded heat map on the template. Whereas the primary motor cortex (M1) was affected to almost 100% in all animals, the degree of lesional overlapping was decreased within the secondary motor cortex (M2) and the primary somatosensory cortex representing the hind limb (estimated 75%) and was even less within the primary somatosensory cortex representing the forelimb (estimated 50%; see FIG. 1C).

Immediately after intervention, as well as before kinematic gait testing (i.e., 3 days after the intervention), all animals exhibited normal cage mobility and no coordination deficits were observed in the use of the affected left forepaw during food uptake. Hematoxylin and eosin staining revealed some variability of electrode placement (see FIG. 2A). In 6 animals, the electrodes were placed close to or within the cuneiform nucleus (Cn; i.e., −7.80 mm from the bregma), whereas 2 animals exhibited a deviation of the tip position into the anterior direction 120 μm from the Cn (i.e., −7.68 mm from bregma). The electrode tip of a third animal was found at the lower right outer border of the Cn, −7.92 mm from bregma. It was decided to keep all animals in the analysis using an intention-to-treat approach, because the optimal mesencephalic site of stimulation was not yet defined.

Histological Analysis of the Neurostimulation Effects

Fluorescent in situ hybridization of consecutive brain sections were performed to visualize the lesion due to the electrode tip, the ChAT+ neurons of the PTg, and c-Fos+ neurons around the stimulation site of each animal. Then, brain sections were mapped onto atlas drawings of the rat brain to show the relationship of electrode sites to cholinergic neurons of the PTg (see FIG. 2A) as well as to the c-Fos+ neurons (see FIG. 2B). The more rostrally localized electrodes (i.e., −7.68 mm anterior—posterior to the bregma) had less effect on gait speed and explain why velocities of 25.4 cm/s and 25.6 cm/s were measured in these 2 animals. Different elements such as cell somata (i.e., glutamatergic as well as cholinergic neurons) as well as axons and dendrites might be activated by applying HFS.

TABLE 1

Comparison of Gait Parameters Using the CatWalk System: Changes in Locomotor Variables Measured Before and After Photothrombotic Stroke

| Parameter | LH | | LF | | RH | | RF | |
|---|---|---|---|---|---|---|---|---|
| | Overall Mean | Constrained Velocities$_a$ | Overall Mean | Constrained Velocities$_a$ | Overall Mean | Constrained Velocities$_a$ | Overall Mean | Constrained Velocities$_a$ |
| Body speed | ↓↓ | ns | ↓↓ | ns | ↓↓ | ↑ | ↓↓ | ns |
| | | ns | | ns | | ↓↓ | | ↓↓ |
| | | ns | | ns | | ns | | ns |
| Step cycle, s | ↑ | ns | ns | ns | ns | ns | ns | ↑ |
| | | ↑↑ | | ns | | ↑↑ | | ↑ |
| | | ns | | ns | | ns | | ns |
| Duty cycle | ↓↓ | ↓ | ns | ns | ↓ | ns | ns | ns |
| | | ↓↓ | | ns | | ↓↓ | | ↓ |
| | | ↓↓ | | ns | | ns | | ns |
| Stride length, cm | ↓↓ | ns | ns | ns | ↓↓ | ns | ↓↓ | ns |
| | | ns | | ns | | ns | | ns |
| | | ns | | ↓↓ | | ns | | ↓↓ |
| Swing speed, cm/s | ↓↓ | ns | ↓↓ | ↓↓ | ↓↓ | ns | ↓↓ | ns |
| | | ↓↓ | | ↓↓ | | ↓↓ | | ↓↓ |
| | | ↓↓ | | ns | | ns | | ns |
| Contact area, cm$_2$ | ↓↓ | ↓↓ | ↓↓ | ↓↓ | ↓↓ | ns | ↓↓ | ns |
| | | ↓↓ | | ↓↓ | | ↓↓ | | ↓↓ |
| | | ↓↓ | | ↓↓ | | ns | | ↓↓ |

A significant increase/decrease of a gait parameter is indicated by ↑/↓ ($p < 0.05$) and ↑↑/↓↓ ($p < 0.01$). Individual numeric values for each parameter and paw are outlined in Supplementary Table S1.
$_a$Slow (top), medium (middle), and fast (bottom).
LF = left forelimb; LH = left hind limb; ns = not significant; RF = right forelimb; RH = right hind limb.

Beam-Walking Test

The behavioral outcome after stroke with and without MLR-HFS was evaluated using the beam-walking test. This test allows evaluation of coordination and integration of paw movements after skilled gait training. On day 7 of training (i.e., before photothrombotic stroke), the average speed of the beam traversing was 22.5±0.8 cm/s. Four days after photothrombotic stroke, all animals demonstrated paw coordination deficits and were unable to traverse the beam without assistance. When MLR-HFS was applied, coordinated locomotion was restored instantaneously and an average speed of 19.7±1.2 cm/s for unassisted beam traversing was recorded (FIG. 3A), which was similar to the gait velocity measured before photothrombotic stroke ($p=0.096$). See Supplementary Video 1-3 of Fluri, F. et al. (2017) Stimulation of the mesencephalic locomotor region for gait recovery after stroke. *Ann Neurol.* 82(5):828-840 for additional videographic data on the effect of MLR-HFS deep brain stimulation on a beam-walking test in a normal control animal (video 1), an animal after photothrombotic stroke (video 2) and MLR-HFS deep brain stimulation of an animal with photothrombotic stroke (video 3).

Changes in locomotor skills and balance were further determined using a 7-point scale. On day 7 of training, mean score was 7; only 1 animal slipped with the forepaw and another with the hind paw when crossing the beam. Four days after photothrombotic stroke, skilled walking on the beam was first tested without HFS in all animals. Only 1 animal was able to maintain balance on the beam; all others fell off the beam. After applying MLR-HFS, skilled locomotion improved significantly in all animals; one of them returned even to a score of 7 (mean), whereas the animal with least effect of MLR-HFS regained a mean score of 4.6 (see FIG. 3B).

To determine whether MLR-HFS exerts a more powerful effect on the fore- or hind-limb, we assessed paw slips and misses off the beam before photothrombotic stroke and thereafter under MLR-HFS conditions. The number of slips measured for fore-paw and hind-paw did not differ before intervention. Whereas no locomotion was visible and thus this parameter was not evaluable after photothrombotic

TABLE 2

Comparison of Gait Parameters Using the CatWalk System: After Photothrombosis without and with Mesencephalic Locomotor Region High-Frequency Stimulation

| Parameter | LH Overall Mean | LH Constrained Velocities$_a$ | LF Overall Mean | LF Constrained Velocities$_a$ | RH Overall Mean | RH Constrained Velocities$_a$ | RF Overall Mean | RF Constrained Velocities$_a$ |
|---|---|---|---|---|---|---|---|---|
| Body speed | ↑↑ | ns | ↑↑ | ns | ↑↑ | ns | ↑↑ | ns |
|  |  | ns |  | ↑↑ |  | ns |  | ↑↑ |
|  |  | ↑↑ |  | ↑ |  | ↑ |  | ↑↑ |
| Step cycle, s | ↓↓ | ns | ↓↓ | ns | ↓ | ns | ns | ns |
|  |  | ↓ |  | ns |  | ns |  | ns |
|  |  | ↓↓ |  | ns |  | ↓ |  | ns |
| Duty cycle | ↓↓ | ns | ns | ns | ns | ns | ↓ | ns |
|  |  | ns |  | ns |  | ns |  | ns |
|  |  | ns |  | ns |  | ns |  | ns |
| Stride length, cm | ↑ | ns | ns | ns | ↑↑ | ns | ↑↑ | ns |
|  |  | ns |  | ns |  | ↑↑ |  | ns |
|  |  | ↑↑ |  | ↑↑ |  | ns |  | ns |
| Swing speed, cm/s | ↑↑ | ns | ↑↑ | ↓ | ↑↑ | ↓ | ↑↑ | ns |
|  |  | ns |  | ns |  | ns |  | ns |
|  |  | ↑↑ |  | ns |  | ns |  | ns |
| Contact area, cm$_2$ | ns | ↓↓ | ↓ | ↓↓ | ns | ↓↓ | ns | ↓↓ |
|  |  | ns |  | ns |  | ns |  | ns |
|  |  | ns |  | ns |  | ns |  | ns |

A significant increase/decrease of a gait parameter is indicated by ↑/↓ ($p < 0.05$) and ↑↑/↓↓ ($p < 0.01$). Individual numeric values for each parameter and paw are outlined in Supplementary Table S1.
$_a$Slow (top), medium (middle), and fast (bottom).

LF = left forelimb; LH = left hind limb; ns = not significant; RF = right forelimb; RH = right hind limb.

stroke without MLR-HFS, significantly fewer paw slips and misses off the beam were observed for the forepaw compared to the hind-paw during MLR-HFS (see FIG. 3C).

No difference in locomotor behavior was found between animals with photothrombotic stroke alone and those subjected to both photothrombosis and electrode implantation (i.e., both groups were no longer able to traverse the beam on day 4 after the intervention), excluding a clinically relevant impact of MLR micro-lesioning by electrode implantation.

TABLE 3

Comparison of Gait Parameters Using the CatWalk System: Before Photothrombosis and Thereafter, When Mesencephalic Locomotor Region High-Frequency Stimulation Was Applied

| Parameter | LH Overall Mean | LH Constrained Velocities$_a$ | LF Overall Mean | LF Constrained Velocities$_a$ | RH Overall Mean | RH Constrained Velocities$_a$ | RF Overall Mean | RF Constrained Velocities$_a$ |
|---|---|---|---|---|---|---|---|---|
| Body speed | ns | ns | ns | ns | ns | ↑↑ | ns | ns |
|  |  | ns |  | ns |  | ↓ |  | ↓ |
|  |  | ↑↑ |  | ↑ |  | ns |  | ↑↑ |
| Step cycle, s | ns | ns | ns | ns | ns | ns | ns | ns |
|  |  | ns |  | ns |  | ↑↑ |  | ns |
|  |  | ↓↓ |  | ↓ |  | ns |  | ns |
| Duty cycle | ↓↓ | ns | ns | ↓ | ↓↓ | ns | ns | ns |
|  |  | ↓↓ |  | ns |  | ↓↓ |  | ↓↓ |
|  |  | ↓↓ |  | ns |  | ns |  | ns |
| Stride length, cm | ns | ns | ns | ns | ns | ns | ns | ns |
|  |  | ns |  | ns |  | ns |  | ns |
|  |  | ↑↑ |  | ns |  | ns |  | ns |
| Swing speed, cm/s | ↓↓ | ns | ns | ↓↓ | ↓↓ | ns | ns | ns |
|  |  | ↓↓ |  | ↓↓ |  | ↓↓ |  | ↓↓ |
|  |  | ↓ |  | ns |  | ns |  | ns |
| Contact area, cm$_2$ | ↓↓ | ↓↓ | ↓↓ | ↓↓ | ↓↓ | ↓↓ | ↓↓ | ↓↓ |
|  |  | ↓↓ |  | ↓↓ |  | ↓↓ |  | ↓↓ |
|  |  | ↓↓ |  | ns |  | ns |  | ↓ |

A significant increase/decrease of a gait parameter is indicated by ↑/↓ ($p < 0.05$) and ↑↑/↓↓ ($p < 0.01$). Individual numeric values for each parameter and paw are outlined in Supplementary Table S1.
$_a$Slow (top), medium (middle), and fast (bottom).
LF = left forelimb; LH = left hind limb; ns = not significant; RF = right forelimb; RH = right hind limb.

SUPPLEMENTAL TABLE S1

|  |  |  | Paw LF |  |  | LH |  |  | RF |  |  | RH |  |  |
|---|---|---|---|---|---|---|---|---|---|---|---|---|---|---|
|  | Time_Point | speed category | N | Mean | SD | N | Mean | SD | N | Mean | SD | N | Mean | SD |
| Body Speed (cm/s) | Before PT | fast | 26 | 64.1 | 6.2 | 40 | 62.6 | 4.7 | 30 | 63.3 | 5.0 | 36 | 64.6 | 6.4 |
|  |  | medium | 77 | 46.5 | 6.2 | 55 | 45.8 | 6.2 | 75 | 45.0 | 6.1 | 59 | 47.7 | 5.5 |
|  |  | slow | 19 | 26.7 | 5.1 | 19 | 26.1 | 4.6 | 18 | 28.2 | 3.4 | 21 | 26.7 | 4.5 |
|  |  | All | 122 | 47.2 | 12.8 | 114 | 48.4 | 13.7 | 123 | 47.0 | 12.2 | 116 | 49.1 | 14.1 |
|  | After PT/ Non-STIM | fast | 7 | 60.6 | 2.0 | 7 | 60.7 | 1.5 | 6 | 60.9 | 3.2 | 10 | 60.9 | 3.3 |
|  |  | medium | 51 | 43.3 | 9.6 | 60 | 43.9 | 11.0 | 56 | 44.6 | 14.1 | 49 | 43.0 | 9.8 |
|  |  | slow | 65 | 27.3 | 5.7 | 65 | 26.0 | 5.6 | 71 | 26.9 | 5.3 | 59 | 28.0 | 6.1 |
|  |  | All | 123 | 35.8 | 12.3 | 132 | 36.0 | 13.5 | 133 | 35.9 | 14.2 | 118 | 37.0 | 12.8 |
|  | After PT/ STIM | fast | 26 | 72.3 | 12.3 | 27 | 69.3 | 9.8 | 28 | 70.0 | 12.1 | 26 | 70.0 | 10.9 |
|  |  | medium | 54 | 44.9 | 6.7 | 52 | 45.2 | 6.3 | 45 | 45.0 | 6.8 | 52 | 46.0 | 6.3 |
|  |  | slow | 30 | 26.5 | 5.3 | 36 | 26.7 | 4.6 | 34 | 27.8 | 4.5 | 30 | 25.6 | 4.6 |
|  |  | All | 110 | 46.3 | 18.3 | 115 | 45.1 | 17.1 | 107 | 46.1 | 17.9 | 108 | 46.1 | 17.6 |
| Step Cycle (s) | Before PT | fast | 25 | 0.3 | 0.0 | 39 | 0.3 | 0.0 | 28 | 0.3 | 0.0 | 34 | 0.2 | 0.0 |
|  |  | medium | 58 | 0.3 | 0.0 | 44 | 0.3 | 0.0 | 57 | 0.3 | 0.0 | 47 | 0.3 | 0.0 |
|  |  | slow | 11 | 0.4 | 0.1 | 9 | 0.4 | 0.0 | 11 | 0.4 | 0.1 | 10 | 0.4 | 0.1 |
|  |  | All | 94 | 0.3 | 0.1 | 92 | 0.3 | 0.1 | 96 | 0.3 | 0.1 | 91 | 0.3 | 0.1 |
|  | After PT/ Non-STIM | fast | 7 | 0.3 | 0.0 | 7 | 0.3 | 0.0 | 6 | 0.3 | 0.0 | 9 | 0.3 | 0.0 |
|  |  | medium | 44 | 0.3 | 0.1 | 57 | 0.3 | 0.1 | 48 | 0.3 | 0.1 | 47 | 0.4 | 0.1 |
|  |  | slow | 44 | 0.5 | 0.1 | 50 | 0.4 | 0.2 | 49 | 0.4 | 0.2 | 43 | 0.4 | 0.1 |
|  |  | All | 95 | 0.4 | 0.1 | 114 | 0.3 | 0.1 | 103 | 0.4 | 0.1 | 99 | 0.4 | 0.1 |
|  | After PT/ STIM | fast | 26 | 0.2 | 0.1 | 27 | 0.2 | 0.1 | 27 | 0.3 | 0.1 | 26 | 0.2 | 0.1 |
|  |  | medium | 42 | 0.3 | 0.0 | 48 | 0.3 | 0.1 | 38 | 0.3 | 0.0 | 48 | 0.3 | 0.1 |
|  |  | slow | 20 | 0.4 | 0.2 | 19 | 0.3 | 0.1 | 16 | 0.5 | 0.1 | 17 | 0.5 | 0.1 |
|  |  | All | 88 | 0.3 | 0.1 | 94 | 0.3 | 0.1 | 81 | 0.3 | 0.1 | 91 | 0.3 | 0.1 |
| Duty Cycle (%) | Before PT | fast | 25 | 54.2 | 10.8 | 39 | 61.9 | 3.7 | 28 | 55.0 | 3.8 | 34 | 54.9 | 14.9 |
|  |  | medium | 58 | 59.2 | 11.1 | 44 | 67.1 | 4.9 | 57 | 60.0 | 7.3 | 47 | 66.9 | 5.2 |
|  |  | slow | 11 | 64.7 | 6.2 | 9 | 73.5 | 4.9 | 11 | 66.3 | 5.3 | 10 | 68.1 | 20.3 |
|  |  | All | 94 | 58.5 | 11.0 | 92 | 65.5 | 5.7 | 96 | 59.3 | 7.1 | 91 | 62.5 | 13.1 |
|  | After PT/ Non-STIM | fast | 7 | 56.6 | 2.4 | 7 | 56.0 | 6.5 | 6 | 55.1 | 2.9 | 9 | 54.8 | 6.4 |
|  |  | medium | 44 | 57.2 | 9.5 | 57 | 53.4 | 17.2 | 48 | 54.9 | 9.5 | 47 | 59.5 | 9.2 |
|  |  | slow | 44 | 60.5 | 10.1 | 50 | 59.4 | 22.5 | 49 | 55.3 | 15.5 | 43 | 58.4 | 22.5 |
|  |  | All | 95 | 58.7 | 9.5 | 114 | 56.2 | 19.5 | 103 | 55.1 | 12.5 | 99 | 58.6 | 16.2 |

SUPPLEMENTAL TABLE S1-continued

|  |  |  | Paw | | | | | | | | | | | |
|---|---|---|---|---|---|---|---|---|---|---|---|---|---|---|
|  |  |  | LF | | | LH | | | RF | | | RH | | |
|  | Time_Point | speed category | N | Mean | SD | N | Mean | SD | N | Mean | SD | N | Mean | SD |
|  | After PT/ | fast | 26 | 49.4 | 9.7 | 27 | 52.3 | 10.5 | 27 | 45.3 | 17.3 | 26 | 51.4 | 14.2 |
|  | STIM | medium | 42 | 56.7 | 8.8 | 48 | 51.7 | 14.3 | 38 | 52.6 | 8.4 | 48 | 57.4 | 7.4 |
|  |  | slow | 20 | 49.5 | 19.7 | 19 | 55.7 | 29.2 | 16 | 57.8 | 4.6 | 17 | 65.0 | 15.4 |
|  |  | All | 88 | 52.9 | 12.7 | 94 | 52.7 | 17.4 | 81 | 51.2 | 12.5 | 91 | 57.1 | 12.2 |
| Stride Length (cm) | Before PT | fast | 25 | 16.9 | 1.4 | 39 | 16.4 | 1.5 | 28 | 16.7 | 1.7 | 34 | 16.5 | 1.1 |
|  |  | medium | 58 | 14.9 | 2.2 | 44 | 15.2 | 1.4 | 57 | 15.0 | 2.1 | 47 | 14.9 | 2.6 |
|  |  | slow | 11 | 12.0 | 2.0 | 9 | 10.5 | 2.2 | 11 | 11.4 | 3.2 | 10 | 10.4 | 4.0 |
|  |  | All | 94 | 15.1 | 2.5 | 92 | 15.2 | 2.3 | 96 | 15.1 | 2.6 | 91 | 15.0 | 2.9 |
|  | After PT/ | fast | 7 | 16.0 | 0.7 | 7 | 16.4 | 1.4 | 6 | 16.2 | 0.3 | 9 | 16.6 | 2.0 |
|  | Non-STIM | medium | 44 | 14.8 | 2.6 | 57 | 14.2 | 3.4 | 48 | 14.3 | 3.3 | 47 | 14.9 | 2.4 |
|  |  | slow | 44 | 12.9 | 2.9 | 50 | 9.9 | 5.6 | 49 | 12.5 | 4.7 | 43 | 11.6 | 4.4 |
|  |  | All | 95 | 14.0 | 2.8 | 114 | 12.5 | 5.0 | 103 | 13.6 | 4.1 | 99 | 13.6 | 3.8 |
|  | After PT/ | fast | 26 | 16.8 | 3.8 | 27 | 16.0 | 4.7 | 27 | 18.3 | 4.5 | 26 | 16.6 | 3.8 |
|  | STIM | medium | 42 | 15.3 | 2.5 | 48 | 15.0 | 4.1 | 38 | 15.4 | 1.8 | 48 | 14.3 | 4.2 |
|  |  | slow | 20 | 11.8 | 4.2 | 19 | 9.1 | 6.0 | 16 | 12.9 | 1.4 | 17 | 11.9 | 3.2 |
|  |  | All | 88 | 15.0 | 3.8 | 94 | 14.1 | 5.3 | 81 | 15.9 | 3.5 | 91 | 14.5 | 4.2 |
| Swing Speed (cm/s) | Before PT | fast | 25 | 149.0 | 24.1 | 39 | 169.6 | 20.0 | 28 | 145.5 | 15.1 | 34 | 157.2 | 21.7 |
|  |  | medium | 58 | 124.7 | 20.5 | 44 | 148.5 | 19.7 | 57 | 122.3 | 20.9 | 47 | 148.4 | 18.6 |
|  |  | slow | 11 | 88.4 | 20.2 | 9 | 111.1 | 19.8 | 11 | 88.6 | 24.6 | 10 | 106.2 | 24.3 |
|  |  | All | 94 | 126.9 | 27.6 | 92 | 153.8 | 26.2 | 96 | 125.2 | 25.8 | 91 | 147.1 | 25.2 |
|  | After PT/ | fast | 7 | 142.4 | 10.0 | 7 | 133.2 | 23.5 | 6 | 134.8 | 13.8 | 9 | 131.7 | 19.7 |
|  | Non-STIM | medium | 44 | 101.3 | 21.4 | 57 | 97.2 | 22.5 | 48 | 98.3 | 23.9 | 47 | 106.3 | 19.8 |
|  |  | slow | 44 | 74.3 | 19.5 | 50 | 67.2 | 29.5 | 49 | 73.5 | 60.0 | 43 | 78.9 | 30.2 |
|  |  | All | 95 | 91.8 | 27.7 | 114 | 86.3 | 31.9 | 103 | 88.6 | 47.4 | 99 | 96.7 | 30.1 |
|  | After PT/ | fast | 26 | 148.6 | 34.5 | 27 | 140.6 | 33.6 | 27 | 149.1 | 74.5 | 26 | 144.3 | 30.9 |
|  | STIM | medium | 42 | 111.8 | 39.5 | 48 | 103.8 | 34.0 | 38 | 102.1 | 20.9 | 48 | 108.8 | 32.0 |
|  |  | slow | 20 | 63.4 | 34.1 | 19 | 56.8 | 26.2 | 16 | 67.4 | 13.3 | 17 | 76.5 | 19.3 |
|  |  | All | 88 | 111.7 | 47.7 | 94 | 104.9 | 43.3 | 81 | 110.9 | 54.3 | 91 | 112.9 | 37.5 |
| Contact Area (cm$^2$) | Before PT | fast | 26 | 1.9 | 0.7 | 40 | 2.4 | 1.0 | 30 | 1.9 | 0.2 | 36 | 2.0 | 0.8 |
|  |  | medium | 77 | 2.2 | 0.8 | 55 | 2.5 | 0.9 | 75 | 1.9 | 0.6 | 59 | 2.4 | 0.6 |
|  |  | slow | 19 | 2.2 | 0.5 | 19 | 3.0 | 1.3 | 18 | 1.7 | 0.6 | 21 | 2.1 | 0.8 |
|  |  | All | 122 | 2.1 | 0.7 | 114 | 2.5 | 1.0 | 123 | 1.9 | 0.5 | 116 | 2.2 | 0.7 |
|  | After PT/ | fast | 7 | 1.3 | 0.2 | 7 | 1.3 | 0.4 | 6 | 1.5 | 0.2 | 10 | 1.2 | 0.7 |
|  | Non-STIM | medium | 51 | 1.2 | 0.9 | 60 | 0.8 | 1.1 | 56 | 1.0 | 0.5 | 49 | 1.0 | 0.7 |
|  |  | slow | 65 | 1.0 | 0.7 | 65 | 0.7 | 0.7 | 71 | 0.9 | 0.6 | 59 | 0.9 | 0.7 |
|  |  | All | 123 | 1.1 | 0.8 | 132 | 0.8 | 0.9 | 133 | 1.0 | 0.5 | 118 | 1.0 | 0.7 |
|  | After PT/ | fast | 26 | 1.2 | 0.6 | 27 | 1.0 | 0.4 | 28 | 1.2 | 0.6 | 26 | 1.0 | 0.6 |
|  | STIM | medium | 54 | 1.2 | 0.7 | 52 | 0.7 | 0.4 | 45 | 1.1 | 0.6 | 52 | 0.8 | 0.5 |
|  |  | slow | 30 | 0.7 | 0.6 | 36 | 0.6 | 0.3 | 34 | 0.9 | 0.5 | 30 | 0.9 | 0.4 |
|  |  | All | 110 | 1.0 | 0.7 | 115 | 0.7 | 0.4 | 107 | 1.1 | 0.6 | 108 | 0.9 | 0.5 |

CatWalk Analyses

Locomotor impairments of fore- and hind-paws after stroke and MLR-HFS—related changes of gait were quantified using the CatWalk system. A similar total number of step cycles before and after photothrombotic stroke was measured (3.9±0.4 vs 3.9±0.3; p=0.86, 95% CI=−0.43 to 0.51). After induction of stroke, MLR-HFS did not change significantly the number of step cycles compared to the nonstimulated state (3.9+0.3 vs 3.7+0.6; p=0.49, 95% CI=−0.40 to 0.77). Gait velocity (mean) was 43.2±6.6 cm/s in "healthy" animals, which was significantly reduced after photothrombosis (31.7±9.0 cm/s; p=0.007, 95% CI=4.11–18.9). When MLR-HFS was applied after photothrombotic stroke, a significant increase in gait velocity was observed (43.8±12.6 cm/s vs 31.7±9.0 cm/s; p=0.04, 95% CI=−23.5 to −0.74).

When comparing gait parameters before and after photothrombosis (without HFS), mean step cycle of the right paws and the left forepaw did not change significantly (Table 1), whereas mean stride length, swing speed, and contact area of all paws (except for the stride length of the left forepaw) were significantly decreased. With respect to stride length, the right paws exhibited the largest deficits. The velocity constrained analysis revealed that these deficits were largely observed at medium gait velocity, but not at slow velocity.

When MLR-HFS was applied after stroke, the overall mean value of step cycle decreased significantly for all paws except for the right forepaw, whereas mean values of swing speed increased significantly (Table 2). Mean values for stride length increased significantly for the right paws, whereas the value of the left hind paw remained unchanged. Mean values of the contact area—a static paw parameter—did not change significantly during MLR-HFS.

Next, we compared gait parameters before photothrombosis and thereafter when MLR-HFS was applied (Table 3). There was no significant difference with respect to step cycle and stride length between the baseline and stimulated stroke condition and duty cycle and swing speed of the forepaws. In contrast, contact area of all 4 paws, as well as duty cycle and swing speed of the hind paws, remained significantly reduced after photothrombotic stroke despite MLR-HFS.

Discussion

In the present study, we examined the effect of MLR-HFS on stroke-related locomotor deficits in rats, which underwent photothrombotic lesioning of the right sensorimotor cortex and implantation of a stimulation electrode into the MLR ipsilateral to the infarction. We verified that the MLR is a site of action of HFS by demonstrating immunohistochemically that glutamatergic as well as cholinergic cells of the dorsal part of the MLR but also cells in adjacent areas expressed c-Fos after MLR-HFS. It is difficult, however, to assign the stimulation effect to particular nuclei or neural elements within this region, because monopolar stimulation with a current intensity of 40 µA, as used in this experiment, may excite neural elements (i.e., myelinated axons) within a radius of 500 to 700 µm from the electrode tip.[33] Which of these elements alone or in combinations contribute to the observed behavioral responses can only be answered in future investigations using cell-type—specific stimulation techniques (e.g., opto- or pharmaco-genetics).

Gait analysis on day 3 after photothrombosis revealed impairment of dynamic gait parameters caused by paresis and—to a lesser extent—by coordination deficits of the contralateral fore- and hind limb during video-kinematic assessment. The deficits were subtle and barely visible during spontaneous cage locomotion. Only challenging tests such as the beam-walking task, requiring nonparetic paws and unimpaired interlimb coordination for maintaining body balance on a narrow path, revealed a clinically relevant locomotor deficit in cortically lesioned animals. Implantation of the stimulating electrode alone had no impact on post stroke gait symptoms, whereas acute HFS of the MLR through the chronically implanted electrode resulted in an immediate restoration of the ability to cross the test beam without assistance.

The most prominent behavioral changes induced by MLR-HFS were an increased gait velocity (+27.6%) as revealed by kinematic analysis as well as a significant amelioration of the skilled walking on the beam. Interestingly, when investigating the left fore- and hind-paw regarding slips off the wooden beam, a significantly higher recovery of the forepaw compared to the hind paw was seen when cortically lesioned animals traversed the beam under MLR-HFS. This might be explained by less lesioning of the forelimb than hind limb representation within sensorimotor cortex as shown by the heat maps. However, the differences of lesion size and site between the somatosensory hind- and fore-limb representation were small, and cortical representations vary widely among individual rats. Alternatively, one might argue that the microelectrode was implanted in a section of the MLR representing the forepaw. Again, this seems unlikely, because previous studies suggest a nonsomatotopic and rather mixed body representation in the MLR.[23] We would therefore like to forward the following alternative hypothesis. Descending projections of the MLR target the medullary and pontine reticular formation.[31]. Recently, Esposito and coworkers have shown that a distinct brainstem nucleus in the ventral part of the medullary reticular formation plays a crucial role in controlling motor activity of forepaws by demonstrating that this brainstem area is connected to a subset of forelimb-innervating spinal motor neurons.[32] Furthermore, their experiments showed that a larger number of brainstem nuclei are connected with forelimb than with hind limb motor neurons,[32] which might explain, in part, the better response of the left forepaw to MLR-HFS. Although the MLR has no direct axonal projections to the somatomotor cortex, it is nevertheless indirectly connected to the cortex via a relay in the thalamus,[33] which might contribute to the modulation of the motor function of the forelimb.

During MLR-HFS, gait velocity increased significantly in cortically lesioned animals. This finding might be of clinical relevance, because independent community ambulation of stroke patients has been shown to require a certain degree of gait velocity (i.e., 0.80 m/s).[34] Additionally, an increase of gait velocity augments the degree of ambulatory activity, which is low in stroke survivors.[35] However, gait velocity induced by MLR-HFS varied greatly among animals, as indicated by the large SD. It is of note that stimulation parameters were always the same in each animal, such that we suspect electrode placement in relation to the individual MLR as an important contributing factor. The anatomical extent of the MLR overlaps with a region ventromedial to the PTg[36], the mesencephalic reticular nucleus, PTg, and Cn in rodents.[19] Most of the electrodes were placed in the center or toward the ventral margin of the Cn. Electrical stimulation of the ventral margin of the Cn has been shown to evoke alternating hind limb movements in pre-collicular-postmamillary decerebrated cats or a change in locomotor behavior from fast walking to gallop in pre-collicular-premamillary decerebrated cats.[37] In the present study, 2 of the electrodes were detected at the far rostral pole of both the Cn/PTg and the MLR. The current—distance relation[30] may result in less intense stimulation of the MLR cell populations controlling locomotor speed (especially the population in the region ventromedial to the PTg) with such an electrode location, which—in turn—would explain a more modest increase of speed after HFS. Additionally, repetitive electrical stimulation of the dorsal part of the PTg in decerebrated cats elicited stepping movements of the hind limb; however, these repetitive stimuli subsequently attenuated locomotion along with a decrease in muscle tone.[37] Altogether, the variability of placement of electrodes in the present study indicates that many sites in the midbrain may have some effect on locomotion, but not necessarily the same, which is in line with the study published by Takakusaki et al.[37]

Altogether, this study demonstrates that MLR-HFS can ameliorate gait disability in a rat model of hemiplegic stroke and that a unilateral stimulation of the MLR (i.e., ipsilateral to the photothrombotic stroke) is sufficient to improve quadrupedal walking. This emphasizes the restorative potential of mesencephalic and spinal motor circuits supporting locomotion, which may be unlocked by neuromodulation therapy. We propose that MLR-HFS shields the mesencephalic and downstream locomotor systems from aberrant cortical input after stroke, and allows for autonomous function of these circuits. The nature and origin of the dysfunctional input activity remains enigmatic. In Parkinson disease and dystonia, a proposed mechanism of DBS is the suppression of abnormal neuronal oscillations binding the basal ganglia—thalamocortical network into a pathological functional state.[38] Whether similar dysfunctional activity arises from the perilesional area after stroke, as a result of maladaptive compensatory changes within the cortical motor network or due to cortical deafferentation of the tonic inhibitory basal ganglia input to the MLR, remains to be elucidated.

Another aspect requiring additional research is the optimal stimulation site within the MLR. The MLR is primarily a functionally defined region at the mesopontine junction; its anatomical substrate is not fully characterized and still remains a matter of debate.[39]

The MLR has been suggested to comprise noncholinergic (i.e., glutamatergic) cells that have been identified within the lateral pontine tegmentum, confined medially by the ventrolateral periaqueductal gray matter and laterally by the PTg.[36] Electrical stimulation at various sites within this region has elicited different forms of locomotor behavior in various species, depending on the stimulation amplitude. Because electrical pulses preferentially activate myelinated fibers ortho-and-antidromically, before small diameter fibers and cell bodies, it is difficult to discern the anatomical substrate of a neurostimulation effect that is often not local, but remote through modulation of pathways rather than nuclei, even if the precise anatomical location of the electrode tip and the electrical field distribution were known.[30] Moreover, a recent study of pedunculopontine neurostimulation in a rat model of Parkinson disease has cast doubt on a prominent locomotor function of the PTg.[40,41] The overall effects of pedunculopontine stimulation in patients have been disappointing, apart from a group in which, by error, a more lateral target site in the mesencephalon was chosen,[42,43] possibly corresponding to the cuneiform nucleus in man.

We note that the number of animals (n=9 per group) is relatively small and histological evaluation revealed a variation of placement of electrodes, which might explain the variable stimulation outcome in this study. Further, the precise location and extent of cortical motor representations for the left fore- and hind-paw have not been evaluated electrophysiologically, which might contribute to a relatively high variability of some postlesional gait parameters. However, such electrophysiological studies require a fenestration of the skull, which—on the other hand—results in a higher burden on animals and thus might influence the locomotor behavior in the acute phase after stroke. Further still, the chosen coordinates for the photothrombotic infarction also encompass somatosensory cortical areas. Very small lesions result in gait impairments that are too mild to be measured even with kinematic analysis (CatWalk). Additionally, all MLR-HFS experiments were conducted using wired neurostimulation by connecting the implanted electrode to an external stimulator. However, because all experiments (especially the CatWalk analysis) were performed by 2 investigators, the wire did not substantially impact the MLR-HFS experiment; animals subjected to photothrombosis only (i.e., not tethered to a neurostimulator) showed no significant differences in locomotor parameters when compared to rats connected to the stimulator via electrical wire (sham stimulation experiment). It is of note that the resistance of cerebral tissue varies widely in the phase shortly after electrode implantation and induction of photothrombosis. Thus, a stimulator with a large voltage compliance range is needed to keep a constant current intensity to compare experiments performed at different time points. The stimulator used in this study is one of the few commercially available stimulator systems with this property and—to our knowledge—there is no portable microstimulator for rats having this feature.

Generated Benefits of an Embodiment of this Invention

We provide a model for MLR-HFS in a rat stroke model, showing an improvement of gait due to the lesioned sensorimotor cortex. The whole procedure is done within short time (<1.5 h) and of high reproducibility, which allows comparing different groups of animals. Since only a few technical components are necessary, the whole procedure is easily comprehensible and of low costs. Using the aforementioned technique, the microelectrode and the plug are well fixed on the skull of the rat and thus stimulation may be extended over 30 days (24/7). Merely by way of example, electrodes made of Pt/Ir are suitable for long-term stimulation, since they demonstrated minimal erosion and do not produce relevant cerebral tissue damage. In contrast to non-invasive methods, invasive stimulation (i) delivers directly electrical current to the target structure, i.e., the MLR, which guarantees that this structure is really stimulated and (ii) might reduce a co-stimulation of other brain structures beside the target area. As a further advantage, a stimulating effect, i.e., improvement of gait is seen immediately when stimulation is turned on. Additionally, the invented model presented here is an ideal tool to investigate the mechanisms underlying DBS and allows determining the most appropriate electrical parameters for DBS. In summary, this model meets a lot of conditions required to translate MLR-DBS from an animal model to humans with motor deficits due to ischemic stroke.

REFERENCES

1. Carmichael S T. Cellular and molecular mechanisms of neural repair after stroke: Making waves. Ann. Neurol. 2006; 59(5):735-742.
2. Murphy T H, Corbett D. Plasticity during stroke recovery: from synapse to behaviour. Nat. Rev. Neurosci. 2009; 10(12):861-872.
3. Carmichael S T. The 3 Rs of Stroke Biology: Radial, Relayed, and Regenerative. Neurotherapeutics 2015; 13(2):348-359.
4. Partridge C, Edwards S. The bases of practice—neurological physiotherapy. Physiother. Res. Int. J. Res. Clin. Phys. Ther. 1996; 1(3):205-208.
5. Bobath B. Adult hemiplegia: evaluation and treatment [Internet]. 3rd ed. Oxford: Oxford Butterworth-Heinemann; 1990. [cited 2016 May 4] Available from: http://trove.nla.gov.au/work/8972936
6. Langhorne P, Coupar F, Pollock A. Motor recovery after stroke: a systematic review. Lancet Neurol. 2009; 8(8): 741-754.
7. Floel A, Cohen L G. Recovery of function in humans: Cortical stimulation and pharmacological treatments after stroke. Neurobiol. Dis. 2010; 37(2):243-251.
8. Barker A T, Jalinous R, Freeston I L. Non-invasive magnetic stimulation of human motor cortex. Lancet 1985; 1(8437):1106-1107.
9. Hao Z, Wang D, Zeng Y, Liu M. Repetitive transcranial magnetic stimulation for improving function after stroke. Cochrane Database Syst. Rev. 2013;(5):CD008862.
10. Rossi S, Hallett M, Rossini P M, et al. Safety, ethical considerations, and application guidelines for the use of transcranial magnetic stimulation in clinical practice and research. Clin. Neurophysiol. Off. J. Int. Fed. Clin. Neurophysiol. 2009; 120(12):2008-2039.
11. Nitsche M A, Cohen L G, Wassermann E M, et al. Transcranial direct current stimulation: State of the art 2008. Brain Stimulat. 2008; 1(3):206-223.
12. Elsner B, Kugler J, Pohl M, Mehrholz J. Transcranial direct current stimulation (tDCS) for improving activities of daily living, and physical and cognitive functioning, in people after stroke. Cochrane Database Syst. Rev. 2016; 3:CD009645.
13. Underwood E. Cadaver study casts doubts on how zapping brain may boost mood, relieve pain [Internet]. Science 2016; [cited 2017 Nov. 14] Available from: http://www.sciencemag.org/news/2016/04/cadaver-study-casts-doubts-how-zapping-brain-may-boost-mood-relieve-pain
14. Levy R M, Harvey R L, Kissela B M, et al. Epidural Electrical Stimulation for Stroke Rehabilitation Results of the Prospective, Multicenter, Randomized, Single-Blinded Everest Trial. Neurorehabil. Neural Repair 2015; 1545968315575613.
15. Volkmann J, Allert N, Voges J, et al. Safety and efficacy of pallidal or subthalamic nucleus stimulation in advanced PD. Neurology 2001; 56(4):548-551.

16. Volkmann J, Allert N, Voges J, et al. Long-term results of bilateral pallidal stimulation in Parkinson's disease. Ann. Neurol. 2004; 55(6):871-875.
17. Volkmann J, Wolters A, Kupsch A, et al. Pallidal deep brain stimulation in patients with primary generalised or segmental dystonia: 5-year follow-up of a randomised trial. Lancet Neurol. 2012; 11(12):1029-1038.
18. Paxinos G, Watson Ch. The rat brain in stereotaxic coordinates. 6th edition. Amsterdam: Academic Press Elsevier; 2007.
19. Roseberry T K, Lee A M, Lalive A L, et al. Cell-Type-Specific Control of Brainstem Locomotor Circuits by Basal Ganglia. Cell 2016; 164(3):526-537.
20. Lindau N T, Banninger B J, Gullo M, et al. Rewiring of the corticospinal tract in the adult rat after unilateral stroke and anti-Nogo-A therapy. Brain 2014; 137(pt 3):739-756.
21. Fluri F, Bieber M, Volkmann J, Kleinschnitz C. Microelectrode Guided Implantation of Electrodes into the Subthalamic Nucleus of Rats for Long-term Deep Brain Stimulation [Internet]. J. Vis. Exp. 2015;(104) [cited 2016 Jan. 25] Available from: http://www.jove.com/video/53066/microelectrode-guided-implantation-electrodes-into-subthalamic
22. Bachmann L C, Matis A, Lindau N T, et al. Deep Brain Stimulation of the Midbrain Locomotor Region Improves Paretic Hindlimb Function After Spinal Cord Injury in Rats. Sci. Transl. Med. 2013; 5:208ral46.
23. Matsumura M, Nambu A, Yamaji Y, et al. Organization of somatic motor inputs from the frontal lobe to the pedunculopontine tegmental nucleus in the macaque monkey. Neuroscience 2000; 98(1):97-110.
24. Hamers F P T, Lankhorst A J, van Laar T J, et al. Automated quantitative gait analysis during overground locomotion in the rat: its application to spinal cord contusion and transection injuries. J Neurotrauma 2001; 18:187-201.
25. Encarnacion A, Horie N, Keren-Gill H, et al. Long-term behavioral assessment of function in an experimental model for ischemic stroke. J Neurosci Methods 2011; 196:247-257.
26. Parkkinen S, Ortega F J, Kuptsova K, et al. Gait impairment in a rat model of focal cerebral ischemia. Stroke Res Treat 2013; 2013:410972.
27. Feeney D M, Gonzalez A, Law W A. Amphetamine, haloperidol, and experience interact to affect rate of recovery after motor cortex injury. Science 1982; 217:855-857.
28. Neckel N D, Dai H, Bregman B S. Quantifying changes following spinal cord injury with velocity dependent locomotor measures. J Neurosci Methods 2013; 214:27-36.
29. Koopmans G C, Brans M, Gomez-Pinilla F, et al. Circulating insulin-like growth factor I and functional recovery from spinal cord injury under enriched housing conditions. Eur J Neurosci 2006; 23:1035-1046.
30. Ranck J B Jr. Which elements are excited in electrical stimulation of mammalian central nervous system: a review. Brain Res 1975; 98:417-440.
31. la Fougere C, Zwergal A, Rominger A, et al. Real versus imagined locomotion: a [18F]-FDG PET-fMRI comparison. Neuroimage 2010; 50:1589-1598.
32. Esposito M S, Capelli P, Arber S. Brainstem nucleus MdV mediates skilled forelimb motor tasks. Nature 2014; 508:351-356.
33. Martinez-Gonzalez C, Bolam J P, Mena-Segovia J. Topographical organization of the pedunculopontine nucleus. Front Neuroanat 2011; 5:22.
34. Perry J, Garrett M, Gronley J K, Mulroy S J. Classification of walking handicap in the stroke population. Stroke 1995; 26:982-989.
35. Michael K M, Allen J K, Macko R F. Reduced ambulatory activity after stroke: the role of balance, gait, and cardiovascular fitness. Arch Phys Med Rehabil 2005; 86:1552-1556.
36. Sherman D, Fuller P M, Marcus J, et al. Anatomical location of the mesencephalic locomotor region and its possible role in locomotion, posture, cataplexy, and parkinsonism. Front Neurol 2015; 6:140.
37. Takakusaki K, Habaguchi T, Ohtinata-Sugimoto J, et al. Basal ganglia efferents to the brainstem centers controlling postural muscle tone and locomotion: a new concept for understanding motor disorders in basal ganglia dysfunction. Neuroscience 2003; 119:293-308.
38. Wichmann T, DeLong M R. Deep brain stimulation for movement disorders of basal ganglia origin: restoring function or functionality? Neurotherapeutics 2016; 13:264-283.
39. Ryczko D, Dubuc R. The Multifunctional Mesencephalic Locomotor Region. Curr Pharm Des 2013; 19:4448-4470.
40. Gut N K, Winn P. The pedunculopontine tegmental nucleus—a functional hypothesis from the comparative literature. Mov Disord 2016; 31:615-624.
41. Gut N K, Winn P. Deep brain stimulation of different pedunculopontine targets in a novel rodent model of parkinsonism. J Neurosci 2015; 35:4792-4803.
42. Stefani A, Lozano A M, Peppe A, et al. Bilateral deep brain stimulation of the pedunculopontine and subthalamic nuclei in severe Parkinson's disease. Brain 2007; 130:1596-1607.
43. Zrinzo L, Zrinzo L V, Hariz M. The pedunculopontine and peripeduncular nuclei: a tale of two structures. Brain 2007; 130:e73.

What is claimed is:

1. A method for treating impaired mobility associated with a brain lesion caused by a stroke or traumatic brain injury in a subject comprising stimulation of mesencephalic locomotor region (MLR) of the subject at a suitable amount or level so as to reverse impaired mobility in the subject, thereby treating impaired mobility associated with a brain lesion in the subject.

2. The method of claim 1, wherein impaired mobility is selected from the group consisting of inability to walk, loss of balance and gait impairment.

3. The method of claim 2, wherein gait impairment comprises any of decreased walking velocity, asymmetric walking pattern, decreased stride length, increased stride width, prolonged swing phase of affected limb, diminished ability to negotiate physical obstacle, diminished ability to adjust walking to changes in terrain, loss of rhythmic movement, diminished ability to move across a beam and a combination thereof.

4. The method of claim 1, wherein the brain lesion is caused by a stroke.

5. The method of claim 4, wherein the stroke is ischemic stroke, hemorrhagic stroke or photothrombotic stroke.

6. The method of claim 1, wherein the brain lesion is located at or about sensorimotor cortex of the subject's brain or its outflow fiber pathways.

7. The method of claim 6, wherein the brain lesion at or about the sensorimotor cortex includes locations at or about the primary motor cortex, premotor cortex, supplementary motor area (SMA), posterior parietal cortex, primary somatosensory cortex and equivalents thereof.

8. The method of claim 6, wherein the brain lesion at or about the sensorimotor cortex includes locations at or about the primary motor cortex, secondary motor cortex, primary somatosensory cortex, and equivalents thereof.

9. The method of claim 1, wherein the brain lesion is located outside of a sensorimotor cortex of the subject's brain.

10. The method of claim 9, wherein the brain lesion located outside of the sensorimotor cortex of the subject's brain is in any of a cerebellum, basal ganglia, subcortical motor nuclei and equivalents thereof.

11. The method of claim 1, wherein the brain lesion is located in left hemisphere of the subject's brain, right hemisphere of the subject's brain or both hemispheres of the subject's brain.

12. The method of claim 1, wherein the brain lesion occurs at a site in the brain which causes impaired mobility.

13. The method of claim 1, wherein the stimulation of mesencephalic locomotor region (MLR) is neuronal activation by an electrical, pharmacological or optogenetic stimulation.

14. The method of claim 13, wherein the electrical stimulation is deep brain stimulation.

15. The method of claim 13, wherein the electrical stimulation comprises low or high-frequency stimulation.

16. The method of claim 15, wherein the electrical stimulation comprises one or more frequencies selected from about 10 to 175 Hz.

17. The method of claim 16, wherein the high-frequency stimulation is a value between about 130 to 175 Hz.

18. The method of claim 13, wherein the electrical stimulation comprises a pulse shape.

19. The method of claim 1, wherein the subject is a mammal which is selected from the group consisting of human, monkey, chimpanzee, ape, lemur, mouse, rat, squirrel, guinea pig, hamster, rabbit, shrew, mole, mink, cat, dog, pig, cow, goat, donkey, horse, sheep, and non-human primate.

20. A method for inhibiting, reducing or reversing a motor deficit in a subject after a stroke comprising administering continuous electrical stimulation to the mesencephalic locomotor region (MLR) of the subject under sufficient conditions so as to inhibit, reduce or reverse the motor deficit of the subject.

21. The method of claim 20, wherein the continuous electrical stimulation is applied to the MLR so as to stimulate the mesencephalic and spinal central pattern generators (CPGs) or shield the mesencephalic and spinal CPGs from aberrant cortical input.

22. The method of claim 20, wherein the MLR is at or near the brainstem of the subject.

23. The method of claim 20, wherein the MLR comprises noncholinergic, predominantly glutamatergic cells localized in the lateral pontine tegmentum, Which form a strip extending from ventrolateral periaqueductal gray matter to a region ventromedial to pedunculopontine tegmental nucleus with ipsilateral predominance or equivalent thereof.

24. The method of claim 20, wherein continuous electrical stimulation to the MLR comprises implantation of electrode close to the MLR.

25. The method of claim 24, wherein implantation of electrode close to the MLR comprises or involves placement of tip of the electrode slightly above dorsal part of the MLR.

26. The method of claim 25, wherein placement of tip of the electrode is ipsilateral to brain lesion associated with the stroke.

27. The method of claim 24, wherein implantation of electrode dose to the MLR comprises or involves placement of tip of the electrode at coordinate about 7.8 mm posterior, 2.0 mm lateral and 5.8 mm ventral to bregma of a rat or equivalent thereof.

28. The method of claim 20, wherein the motor deficit is a gait impairment, inability to walk, or loss of balance.

29. The method of claim 20, wherein the subject is a human, mouse, rat, squirrel, guinea pig, hamster, rabbit, shrew, mole, mink, cat or dog.

* * * * *